US007220577B2

(12) United States Patent
Zolotukhin

(10) Patent No.: US 7,220,577 B2
(45) Date of Patent: May 22, 2007

(54) MODIFIED AAV

(75) Inventor: Sergei Zolotukhin, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 200 days.

(21) Appl. No.: 10/651,828

(22) Filed: Aug. 28, 2003

(65) Prior Publication Data

US 2004/0180440 A1 Sep. 16, 2004

Related U.S. Application Data

(60) Provisional application No. 60/407,583, filed on Aug. 28, 2002.

(51) Int. Cl.
*C12N 15/86* (2006.01)
*C12N 15/864* (2006.01)
*C12N 15/63* (2006.01)
*C12N 15/64* (2006.01)
*A61K 48/00* (2006.01)

(52) U.S. Cl. .............................. 435/320.1; 435/235.1; 536/23.1; 536/23.4; 536/23.7; 536/23.72

(58) Field of Classification Search ..................... None
See application file for complete search history.

(56) References Cited

U.S. PATENT DOCUMENTS

2002/0045264 A1* 4/2002 During et al. .............. 435/456
2003/0138772 A1* 7/2003 Gao et al. ....................... 435/5

OTHER PUBLICATIONS

Wu et al. Adeno-Associated Virus Vector-Mediated Transgene Integration into Neurons and Other Nondiving Cell Targets. Journal of Virology. Jul. 1998, vol. 72, No. 7, pp. 5919-5926.

Wu et al. Mutational Analysis of the Adeno-Associated Virus Type 2 (AAV2) Capsid Gene and Construction of AAV2 Vectors with Altered Tropism. Journal of Virology. Sep. 2000, vol. 74, No. 18, pp. 8635-8647.

Grifman et al. Incorporation of Tumor-Targeting Peptides into Recombinant Adeno-Associated Virus Capsids. Molecular Therapy. Jun. 2001, vol. 3, pp. 964-975.

Girod et al. Genetic Capsid Modification Allows Efficient Re-Targeting of Adeno-Associated Virus Type-2. Nature Medicine. Sep. 1999, vol. 5, pp. 1052-1056.

Xie et al. The Atomic Structure of Adeno-Associated Virus (AAV-2), A Vector for Human Gene Therapy. Proceedings of the National Academy of Sciences. Aug. 2002, vol. 99, No. 16, pp. 10405-10410.

Rabinowitz et al. Building a Better Vector: The Manipulation of AAV Virions. Virology. 2000, vol. 278, pp. 301-308.

Monahan et al. AAV Vectors: Is Clinical Success on the Horizon? Gene Therapy. 2000, vol. 7, pp. 24-30.

He et al., A Simplified System for Generating Recombinant Adenoviruses. Proceedings of the National Academy of Sciences. Mar. 1998, vol. 95, pp. 2509-2514.

Xiao et al. Production of High-Titer Recombinant Adeno-Associated Virus Vectors in the Absence of Helper Adenovirus. Journal of Virology. Mar. 1998, vol. 72, No. 3, pp. 2224-2232.

Davidson et al. Recombinant Adeno-Associated Virus Type-2,4 and 5 Vectors: Transduction of Variant Cell Types and Regions in the Mammalian Central Nervous System. Proceedings of the National Academy of Sciences. vol. 97, No. 7, pp. 3428-3432.

* cited by examiner

*Primary Examiner*—David Guzo
(74) *Attorney, Agent, or Firm*—Akerman Senterfitt; Nicholas A. Zachariades

(57) ABSTRACT

Libraries of modified AAV cap genes are generated by synthesizing modified cap genes using degenerate oligonucleotides. Combinatorial libraries of virions composed of modified (e.g., chimeric), replication-competent AAV vectors and modified Cap proteins are also produced. Helper vectors are described that encode AAV Rep protein, modified Cap proteins, and Ad proteins. The helper vectors are used to produce stocks of virions composed of modified (e.g., chimeric) capsids and rAAV vectors.

56 Claims, 4 Drawing Sheets

SEQUENCE LISTING

```
<160> NUMBER OF SEQ ID NOS: 10

<210> SEQ ID NO 1
<211> LENGTH: 7
<212> TYPE: PRT
<213> ORGANISM: Artificial
<220> FEATURE:
<223> OTHER INFORMATION: Synthetic Peptide Sequence
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (6)..(7)
<223> OTHER INFORMATION: Xaa can be any naturally occurring amino acid

<400> SEQUENCE: 1

Xaa Xaa Leu Ser Pro Xaa Xaa
1               5


<210> SEQ ID NO 2
<211> LENGTH: 7
<212> TYPE: PRT
<213> ORGANISM: Artificial
<220> FEATURE:
<223> OTHER INFORMATION: Synthetic Peptide Sequence
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (6)..(7)
<223> OTHER INFORMATION: Xaa can be any naturally occurring amino acid

<400> SEQUENCE: 2

Xaa Xaa Leu Leu Val Xaa Xaa
1               5


<210> SEQ ID NO 3
<211> LENGTH: 7
<212> TYPE: PRT
```

-continued

```
<213> ORGANISM: Artificial
<220> FEATURE:
<223> OTHER INFORMATION: Synthetic Peptide Sequence
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (6)..(7)
<223> OTHER INFORMATION: Xaa can be any naturally occurring amino acid

<400> SEQUENCE: 3

Xaa Xaa Glu Gly Gly Xaa Xaa
1               5


<210> SEQ ID NO 4
<211> LENGTH: 7
<212> TYPE: PRT
<213> ORGANISM: Artificial
<220> FEATURE:
<223> OTHER INFORMATION: Synthetic Peptide Sequence
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (6)..(7)
<223> OTHER INFORMATION: Xaa can be any naturally occurring amino acid

<400> SEQUENCE: 4

Xaa Xaa Leu Val Ser Xaa Xaa
1               5


<210> SEQ ID NO 5
<211> LENGTH: 8
<212> TYPE: PRT
<213> ORGANISM: Artificial
<220> FEATURE:
<223> OTHER INFORMATION: Synthetic Peptide Sequence
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (7)..(8)
<223> OTHER INFORMATION: Xaa can be any naturally occurring amino acid

<400> SEQUENCE: 5

Xaa Xaa Thr Gly Gly Glu Xaa Xaa
1               5


<210> SEQ ID NO 6
<211> LENGTH: 7
<212> TYPE: PRT
<213> ORGANISM: Artificial
<220> FEATURE:
<223> OTHER INFORMATION: Synthetic Peptide Sequence
<220> FEATURE:
<221> NAME/KEY: misc_feature
<222> LOCATION: (1)..(7)
<223> OTHER INFORMATION: Xaa can be any naturally occurring amino acid

<400> SEQUENCE: 6

Xaa Xaa Xaa Xaa Xaa Xaa Xaa
1               5


<210> SEQ ID NO 7
<211> LENGTH: 4
```

-continued

```
<212> TYPE: PRT
<213> ORGANISM: Artificial
<220> FEATURE:
<223> OTHER INFORMATION: Synthetic Peptide Sequence

<400> SEQUENCE: 7

Thr Gly Gly Glu
1


<210> SEQ ID NO 8
<211> LENGTH: 22
<212> TYPE: DNA
<213> ORGANISM: Artificial
<220> FEATURE:
<223> OTHER INFORMATION: Synthetic Oligonucleotides

<400> SEQUENCE: 8

cgcgaaaaac tgattcagag aa                                              22


<210> SEQ ID NO 9
<211> LENGTH: 19
<212> TYPE: DNA
<213> ORGANISM: Artificial
<220> FEATURE:
<223> OTHER INFORMATION: Synthetic Oligonucleotides

<400> SEQUENCE: 9

gaccgcgaac cagtttggc                                                  19


<210> SEQ ID NO 10
<211> LENGTH: 18
<212> TYPE: DNA
<213> ORGANISM: Artificial
<220> FEATURE:
<223> OTHER INFORMATION: Synthetic Oligonucleotides

<400> SEQUENCE: 10

ccgcgggatc gagccgac                                                   18
```

MODIFIED AAV

CROSS-REFERENCE TO RELATED APPLICATIONS

The present application claims the priority of U.S. provisional patent application Ser. No. 60/407,583 filed on Aug. 28, 2002.

STATEMENT AS TO FEDERALLY SPONSORED RESEARCH

The invention was made with U.S. government support under grant numbers HL051811 and NS036302 awarded by the National Institutes of Health. The U.S. government may have certain rights in the invention.

FIELD OF THE INVENTION

The invention relates to the fields of molecular biology, gene therapy, and virology. More particularly, the invention relates to compositions and methods for (i) producing modified Adeno-Associated Virus (AAV) cap genes and combinatorial libraries of chimeric AAV vectors and virions; (ii) selecting for virions displaying cell-specific tropisms; and (iii) producing helper vectors containing modified, chimeric AAV cap genes.

BACKGROUND OF THE INVENTION

Recombinant Adeno-Associated Viruses (rAAV) based on AAV serotype 2 (AAV2) have become recognized as vehicles of choice for many gene-delivery applications for several reasons. Among these, AAV2 are able to transduce and cause persistent transgene expression in several different cell types including both dividing and quiescent cells without normally causing pathology or a vigorous cell-mediated immune response (reviewed in He et al., Proceedings of the National Academy of Sciences, 95:2509–2514, 1998; Monahan et al., Gene Ther. 7:24–30, 2000; and Rabinowitz et al., Virology 278:301–308, 2000). Although the broad host cell tropism of rAAV2 virions is advantageous in many situations, it is often undesirable in others. In addition, the broad cell tropism of rAAV2 often requires an impractically large dose of virions to induce a therapeutic effect as virions infect both target and non-target cells. A major goal in this field has thus been to develop rAAV that selectively target only a particular cell type or tissue. Such cell-selective rAAV would reduce or eliminate non-target cell transduction and also thereby reduce the viral dose required to cause a therapeutic effect.

Producing cell- or tissue-specific AAV virions, however, has proven to be a difficult undertaking. A major reason for this is that until very recently (Xie et al, Proceedings of the National Academy of Sciences, 2002, v. 99, p.10405–10410), no structure had been resolved for any AAV serotype. The structural information that was available was inferred from parvovirus sequence homologies (Girod et al., Nat. Med. 5:1052–1056, 1999; and Grifman et al., Mol. Ther.3:964–975, 2001) and mutational analyses of the AAV2 capsid gene (cap). Through the latter technique, the amino acid residues of AAV2 that are critical for binding to AAV's primary cellular receptor (the heparan sulfate proteoglycan receptor) were identified. Despite this advance, methods for altering AAV tropism have not been optimized. For example, some rAAV virions made to express particular homing peptides exhibit packaging problems. Such problems underscore the need for a new, more practical approach for creating rAAV with restricted tropisms.

SUMMARY

The invention relates to the construction of chimeric replication-competent (rcAAV) vectors encoding modified Cap proteins, virions containing chimeric rcAAV vectors, virions composed of chimeric capsids (e.g., capsids containing a degenerate, recombined, shuffled or otherwise modified Cap protein), chimeric rcAAV virions having cell- and tissue-specific tropisms, combinatorial vector and virion libraries, and AAV helper vectors encoding chimeric Cap proteins. Combinatorial libraries are generated using degenerate synthetic oligonucleotides that result in the incorporation of every polymorphism within the seven loops of the AAV capsid genes from serotypes 1 through 8. Using a combinatorial library of the invention, virions with cell- and tissue-specific tropisms can be selected.

The invention also relates to the construction of helper vectors that provide AAV Rep and Cap proteins for producing stocks of virions composed of an rAAV vector (e.g., a vector encoding a therapeutic gene) and a chimeric capsid (e.g., a capsid containing a degenerate, recombined, shuffled or otherwise modified Cap protein) that has a cell- or tissue-specific tropism. DNA from a selected population of virions having a desired cell- or tissue-specific tropism can be used to produce modified capsid genes encoding a particular cell-type tropism. Diverse libraries of multiple recombinants can thus be made from which virions with a desired tropism can be selected. The virions composed of modified, chimeric capsids having cell- and tissue-specific tropisms can be used as sources of gene delivery vehicles that exhibit high specificity for particular cells and tissues.

Accordingly, the invention features a non-naturally occurring nucleic acid that includes: (A) a first nucleotide sequence encoding at least one AAV Rep protein; and (B) a second nucleotide sequence encoding at least one AAV Cap protein, wherein the second nucleotide sequence comprises (i) a polynucleotide encoding a portion of a Cap protein found in an AAV of a first serotype but not in an AAV of a second serotype differing from the first serotype and (ii) a polynucleotide encoding a portion of a Cap protein found in the AAV of the second serotype, but not in the AAV of the first serotype.

The invention also includes a vector library that includes at least a first vector and a second vector. The first vector including the foregoing non-naturally occurring nucleic acid, and the second vector differing from the first vector by at least one nucleotide.

In another aspect, the invention features an AAV virion that includes a nucleic acid having: (A) a first nucleotide sequence encoding at least one AAV Rep protein; (B) a second nucleotide sequence encoding at least one AAV Cap protein, wherein the second nucleotide sequence comprises (i) a polynucleotide encoding a portion of a Cap protein found in an AAV of a first serotype but not in an AAV of a second serotype differing from the first serotype, and (ii) a polynucleotide encoding a portion of a Cap protein found in the AAV of the second serotype, but not in the AAV of the first serotype; and (C) a first and a second AAV TR, wherein the first and the second nucleotide sequences are interposed between the first and the second AAV TRs. An additional virion of the invention further includes at least one AAV Cap protein encoded by the second nucleotide sequence.

Yet another AAV virion of the invention includes: a nucleic acid having a first AAV TR; a second AAV TR; and a non-AAV nucleic acid interposed between the first AAV TR and the second AAV TR; and (B) at least one AAV Cap protein encoded by a nucleotide sequence including nucleic acid sequences from AAVs of at least a first serotype and a second serotype differing from the first serotype.

The invention also includes a virion library having at least a first AAV virion and a second AAV virion. The first AAV virion features a nucleic acid having: (A) a first nucleotide sequence encoding at least one AAV Rep protein; (B) a second nucleotide sequence encoding at least one AAV Cap protein, wherein the second nucleotide sequence includes (i) a polynucleotide encoding a portion of a Cap protein found in an AAV of a first serotype but not in an AAV of a second serotype differing from the first serotype, and (ii) a polynucleotide encoding a portion of a Cap protein found in the AAV of the second serotype, but not in the AAV of the first serotype; and (C) a first and a second AAV TR, wherein the first and the second nucleotide sequences are interposed between the first and the second AAV TRs, and the second AAV virion comprising a nucleic acid not comprised within the first AAV virion. An additional virion library of the invention includes first and second virions that further include at least one AAV Cap protein encoded by the second nucleotide sequence, the second AAV virion including a Cap protein not included within the first AAV virion.

A further aspect of the invention is a method that includes the steps of: (A) providing a first polynucleotide and a second polynucleotide, the first and second polynucleotides including an identical nucleotide sequence encoding at least a portion of an AAV Cap protein; (B) mutating the first and second polynucleotides to generate a plurality of mutants, wherein each mutant comprises a nucleotide sequence encoding a portion of a Cap protein found in an AAV of a first serotype but not in an AAV of a second serotype differing from the first serotype; and C) placing each of the plurality of mutants into vectors to form a plurality of vectors. This method can also include one or more of the following steps: (D) introducing at least one of the vectors into a first host cell; (E) providing rep and cap gene products having WT functional activity to the first host cell; (F) culturing the first host cell under conditions that allow production of a first population of virions containing the vectors, wherein the virions include at least one WT AAV Cap protein; (F) harvesting the first population of virions from the first host cell; (G) infecting a second host cell with the first population of virions under conditions that allow production of a second population of virions, wherein each virion of the second population of virions includes: (i) a first nucleotide sequence encoding at least one AAV Rep protein; (ii) a second nucleotide sequence encoding at least one AAV Cap protein, wherein the nucleotide sequence includes nucleic acid sequences from at least the first AAV serotype and the second AAV serotype; and (iii) at least one AAV Cap protein encoded by the second nucleotide sequence; (H) harvesting the second population of virions from the second host cell; (I) introducing the second population of virions into a target cell; (J) culturing the target cell under conditions that allow production of a third population of virions; (K) harvesting the third population of virions from the target cell; (L) isolating a nucleic acid from the third population of virions that encodes an AAV Cap protein; (M) determining the sequence of the nucleic acid isolated from the third population of virions; (N) placing the nucleic acid isolated from the third population of virions into a second vector; (O) introducing the second vector into a third host cell; (P) introducing into the third host cell a nucleotide sequence encoding at least one AAV Rep protein; (O) providing to the third host cell at least one molecule having helper function; (R) introducing into the third host cell a nucleic acid including: (i) a first AAV TR, (ii) a second AAV TR, and (iii) a non-AAV nucleic acid interposed between the first AAV TR and the second AAV TR; (S) culturing the third host cell under conditions that allow production of virions, wherein the virions contain the nucleic acid of step (R); and (T) harvesting virions from the cell.

Unless otherwise defined, all technical terms used herein have the same meaning as commonly understood by one of ordinary skill in the art to which this invention belongs. Commonly understood definitions of molecular biology terms can be found in Rieger et al., Glossary of Genetics: Classical and Molecular, 5th edition, Springer-Verlag: New York, 1991; and Lewin, Genes V, Oxford University Press: New York, 1994. Commonly understood definitions of virology terms can be found in Granoff and Webster, Encyclopedia of Virology, 2nd edition, Academic Press: San Diego, Calif., 1999; and Tidona and Darai, The Springer Index of Viruses, 1st edition, Springer-Verlag: New York, 2002. Commonly understood definitions of microbiology can be found in Singleton and Sainsbury, Dictionary of Microbiology and Molecular Biology, 3rd edition, John Wiley & Sons: New York, 2002.

As used herein, the phrase "nucleic acid" means a chain of two or more nucleotides such as RNA (ribonucleic acid) and DNA (deoxyribonucleic acid). The phrases "cap nucleic acid," "cap gene," and "capsid gene" as used herein mean a nucleic acid that encodes a Cap protein. Examples of cap nucleic acids include "wild-type" (WT) Cap-encoding nucleic acid sequences from AAV serotypes 1, 2, and 5; a native form cap cDNA; a nucleic acid having sequences from which a cap cDNA can be transcribed; and/or allelic variants and homologs of the foregoing.

As used herein, "protein" or "polypeptide" mean any peptide-linked chain of amino acids, regardless of length or post-translational modification, e.g., glycosylation or phosphorylation. By the phrase "Cap protein" is meant an expression product of a cap nucleic acid from any serotype, such as a native Cap protein from serotypes 1, 2, 3, 4, 5, 6, 7, or 8; or a protein that shares at least 65% (but preferably 75, 80, 85, 90, 95, 96, 97, 98, or 99%) amino acid sequence identity with one of the foregoing and displays a functional activity of a native Cap protein. A "functional activity" of a protein is any activity associated with the physiological function of the protein. For example, functional activities of a native Cap protein may include the ability to form a capsid.

When referring to a nucleic acid molecule or polypeptide, the term "native" refers to a naturally-occurring (e.g., a WT) nucleic acid or polypeptide.

The phrase "expression control sequence" refers to any genetic element (e.g., polynucleotide sequence) that can exert a regulatory effect on the replication or expression (transcription or translation) of another genetic element. Common expression control sequences include promoters, polyadenylation (polyA) signals, transcription termination sequences, upstream regulatory domains, origins of replication, internal ribosome entry sites (IRES), enhancers, and the like. A "tissue specific expression control sequence" is one that exerts a regulatory effect on the replication or expression (transcription or translation) of another genetic element in only one type of tissue or a small subset of tissues.

A first nucleic acid sequence is "operably" linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked nucleic acid sequences are contiguous and, where necessary to join two protein coding regions, in reading frame.

As used herein, the term "vector" refers to a nucleic acid molecule capable of transporting another nucleic acid to which it has been linked, e.g., a plasmid. One type of preferred vector is an episome, i.e., a nucleic acid capable of extra-chromosomal replication. Preferred vectors are those capable of autonomous replication and/or expression of nucleic acids to which they are linked. An "rAAV vector" is a recombinant AAV-derived nucleic acid containing at least one terminal repeat (TR) sequence.

By use of "virion" is meant a virus particle that contains a nucleic acid and a protein coat (capsid). An "rAAV virion" is a virion that includes nucleic acid sequences and/or proteins derived from a rAAV vector.

As used herein, the terms "terminal repeat" or "TR" mean a nucleic acid sequence derived from an AAV that is required in cis for replication and packaging of AAV.

By the term "pseudotyped" is meant a nucleic acid or genome derived from a first AAV serotype that is encapsidated (packaged) into an AAV capsid containing at least one AAV Cap protein of a second serotype differing from the first serotype.

As used herein, the term "rcAAV vector" refers to a replication-competent AAV-derived nucleic acid capable of DNA replication in a cell without any additional AAV genes or gene products.

As used herein, the term "chimeric rcAAV" refers to a replication-competent AAV-derived nucleic acid containing at least one nucleotide sequence that 1) encodes an AAV protein and 2) differs from the corresponding native nucleotide sequence in one or more bases.

By the phrase "helper function" is meant a functional activity performed by a nucleic acid or polypeptide that is derived from a virus such as Adenovirus (Ad) or herpesvirus and that facilitates AAV replication in a host cell.

The term "library" refers to a collection of elements that differ from one another in at least one aspect. For example, a vector library is a collection of at least two vectors that differ from one another by at least one nucleotide. As another example, a "virion library" is a collection of at least two virions that differ from one another by at least one nucleotide or at least one capsid protein.

By the term "seed library" is meant a pool of AAV virions composed of chimeric rcAAV vectors encapsidated into AAV capsids of a single serotype.

As used herein, the term "master" library refers to a pool of rAAV virions composed of chimeric rcAAV vectors encapsidated in cognate chimeric capsids (e.g., capsids containing a degenerate or otherwise modified Cap protein).

The phrase "helper function" refers to a functional activity performed by a nucleic acid or polypeptide derived from a helper virus such as Adenovirus (Ad) or Herpesvirus that promotes AAV replication in a host cell.

Although methods and materials similar or equivalent to those described herein can be used in the practice or testing of the present invention, suitable methods and materials are described below. All publications, patent applications, patents and other references mentioned herein are incorporated by reference in their entirety. In the case of conflict, the present specification, including definitions will control. The particular embodiments discussed below are illustrative only and not intended to be limiting.

DETAILED DESCRIPTION

Figure 1:
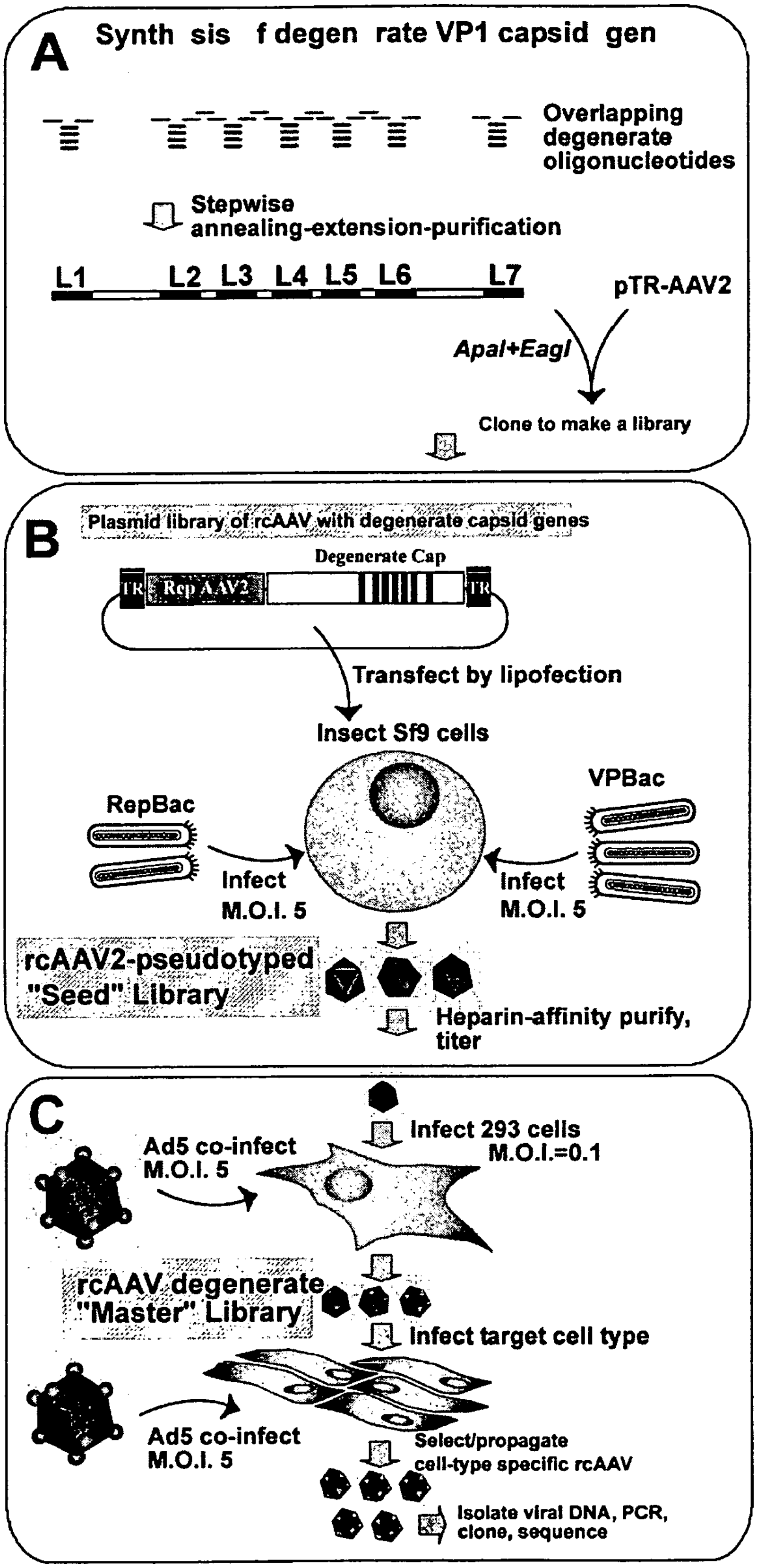
FIG. 1 is a schematic overview of a method of preparing chimeric rcAAV. (A) preparation of degenerate oligonucleotide synthesis-mutagenized fragments of WT AAV2 capsid gene sequences; (B) rescue, replication and pseudo-packaging of degenerate rAAV vectors into AAV2 capsids and the resultant "seed" library. (C) illustrates production of a "master" library by infecting 293 cells with the seed library.

The invention relates to the construction and use of combinatorial rAAV libraries that may be used to select rAAV with a desired cell- or tissue-specific tropism and to generate helper vectors that may be used to propagate rAAV having a desired cell- or tissue-specific tropism. In a preferred embodiment of the invention, the rAAV libraries of the invention are composed of rAAV vectors and virions containing a modifed cap gene such as a chimeric cap gene (e.g., a cap gene that has been modified to contain nucleotide sequences from more than one AAV serotype). To construct a combinatorial library of chimeric rAAV vectors, several steps are followed. First, cloned WT AAV capsid genes are modified in vitro using a suitable mutagenesis protocol. A preferred mutagenesis protocol involves the synthesis of degenerate capsid genes using degenerate oligonucleotides (Coco et al., Nature Biotechnology 20:1246–1250, 2003). Using degenerate oligonucleotide synthesis, any desired nucleotide or amino acid substitution can be incorporated into WT AAV capsid gene sequences. For example, polymorphisms from AAV serotypes 1–8 can be incorporated into a WT AAV2 cap sequence to generate a pool of degenerate AAV capsid genes containing sequences from AAV serotypes 1–8.

To create a combinatorial library of chimeric rAAV virions (chimeric rAAV vectors encapsidated within capsids composed of cognate modified Cap proteins encoded by the rAAV vector), the pool of modified chimeric capsid genes are inserted into an rAAV vector that, if transduced into a mammalian cell, is capable of replication in the presence of helper functions (e.g., Ad or Herpesvirus helper functions). The pool of rAAV vectors, each containing a modified cap gene, is transfected into a suitable host cell (e.g., using a liposome-mediated technique) such as an insect cell (e.g., SF9 cells). These cells are then co-infected with two recombinant baculoviruses (RepBac and VPBac) that provide wild-type rep and cap gene products (FIG. 1B). The use of a heterologous system (insect cells) at this step silences WT AAV genome promoters and aborts the expression of the modified capsid genes since WT AAV2 promoters are either silent or very inefficient in insect cells. This aspect of the method is important for achieving packaging of the chimeric rAAV vectors into WT AAV2 capsids. If the modified cap genes were expressed in the insect cells, degenerate capsids would be assembled from a pool of thousands of individual VP-proteins, encoded by one out of a pool of thousands of degenerate capsid genes. The resulting library would consist of vectors containing degenerate capsid genes pseudotyped into capsids not necessarily derived from the encapsidated genome. This would not allow for the subsequent selection and propagation of a particular cell type-specific capsid. Therefore, at this stage of propagating seed library virions, it is preferred that all chimeric rAAV vectors are packaged in WT capsids from a single serotype (e.g., WT AAV2 capsids). Accordingly, a heterologous system (e.g., insect cells) which blocks expression of degenerate capsid genes but that provides expression of requisite WT rep and cap genes (e.g., via recombinant helper baculoviruses whose promoters drive the expression of WT rep and cap genes) is utilized.

This arrangement provides for the rescue, replication and cross-packaging (pseudopackaging) of rAAV vectors containing degenerate capsid genes into AAV2 capsids. The seed library (FIG. 1B) is subsequently purified using a suitable purification protocol (e.g., iodixanol gradient centrifugation followed by heparin affinity chromatography). Such a purified library is titered for physical as well as infectious virions (particles) using standard techniques.

In the exemplary embodiment, all virions of the seed library have identical AAV2 capsids. Each virion, however, harbors a degenerate capsid gene. In order to make a master library, cells permissive to AAV2 infection (e.g., 293 cells) are infected with the seed library at a low MOI (e.g., 0.1) (FIG. 1C). The low MOI ensures that most of the cells are infected with a single rcAAV vector-containing virion. In addition, cells are co-infected with a helper virus (e.g., Ad) to provide helper functions. As a result of a productive infectious cycle, every cell infected with a virion containing a rcAAV vector produces a unique rcAAV vector and capsids encoded by this single degenerate (chimeric) rcAAV vector. The resultant master library consists of chimeric (e.g., degenerate) virions made of chimeric capsids encapsidating cognate chimeric (e.g., the same degenerate) capsid genes (shown in FIG. 1C as AAV virions having different surface antigen tags).

The master library is used to infect target cells or tissues to select for virions with particular tropisms (e.g., a desired cell- or tissue-specific tropism). A master library of the invention is a useful source of gene therapy virions with individual specificities for particular cell and tissue types. The use of cell- or tissue-specific gene therapy virions produced by methods of the invention reduces the viral dose required and also reduces potential side effects in the recipient.

As an example, to select for rAAV virions with a modified tropism, cells normally non-permissive to AAV infection are infected with the rAAV virions. Only those modified rAAV virions exhibiting a tropism to the non-permissive cell type will result in a productive infection. Similarly, rAAV virions that exhibit an increased or decreased ability to infect a particular cell or tissue type can be selected. Selected virions that can specifically target diseased cells or tissues over non-diseased cell or tissues are useful for treating various diseases.

Chimeric rcAAV vectors selected from the master library for a cell- or tissue-specific tropism are used to produce helper vectors encoding modified capsid proteins with tropisms to the same cell or tissue. Helper vectors encoding modified Cap proteins are used to introduce at least one modified AAV cap gene into a host cell in a method of generating chimeric virions having a desired cell- or tissue-specific tropism. The modified cap gene expresses a cognate Cap protein that supports the encapsidation of a rAAV vector within an rAAV capsid. In addition to at least one modified cap gene, helper vectors can contain a nucleotide sequence encoding one or more AAV Rep proteins. rAAV vectors packaged using helper vectors of the invention can contain non-AAV nucleic acids, e.g., therapeutic genes. Using such helper vectors, gene therapy viruses that encode a therapeutic gene and infect a particular cell type can be produced. In addition to targeting a specific cell or tissue type, the chimeric virions selected from the combinatorial library offer the further benefit of not invoking a pre-existing immune response in a patient receiving the therapeutic chimeric virions. As the chimeric virions do not exist in nature, the patient's immune response will not have previously encountered the virions. This obviates the pre-screening of a patient for the presence of pre-existing antibodies to the virions prior to administering the chimeric rAAV-based therapy.

The various embodiments described herein are presently preferred variations of the invention. Nonetheless, from the description of these embodiments, other aspects of the invention can be made and/or practiced based on the description provided below.

Biological Methods

Methods involving conventional molecular biology techniques are described herein. Such techniques are generally known in the art and are described in detail in methodology treatises such as Molecular Cloning: A Laboratory Manual, 3rd ed., vol. 1–3, ed. Sambrook et al., Cold Spring Harbor Laboratory Press, Cold Spring Harbor, N.Y., 2001; and Current Protocols in Molecular Biology, ed. Ausubel et al., Greene Publishing and Wiley-Interscience, New York, 1992 (with periodic updates). Methods for chemical synthesis of nucleic acids are discussed, for example, in Beaucage and Carruthers, Tetra. Letts. 22:1859–1862, 1981, and Matteucci et al., J. Am. Chem. Soc. 103:3185, 1981. Chemical synthesis of nucleic acids can be performed, for example, on commercial automated oligonucleotide synthesizers. Conventional methods of gene transfer and gene therapy can also be adapted for use in the present invention. See, e.g., Gene Therapy: Principles and Applications, ed. T. Blackenstein, Springer Verlag, 1999; Gene Therapy Protocols (Methods in Molecular Medicine), ed. P. D. Robbins, Humana Press, 1997; and Retro-vectors for Human Gene Therapy, ed. C. P. Hodgson, Springer Verlag, 1996.

AAV Serotypes

The AAV nucleic acids (e.g., rep and cap), proteins, vectors, and virions used in the invention may be derived from any of several AAV serotypes including 1, 2, 3, 4, 5, 6, 7, and 8. Genes from these serotypes can be isolated using standard methods (Chiorini et al., J Virol 73:1309–19, 1999; Rutledge et al., J Virol 72:309–19, 1998; Xiao et al., J. Virol.

73:3994–4003, 1999; Muramatsu et al., Virology 221:208, 1996; and Chiorini, et al., J. Virol. 71:6823, 1997; Sambrook and Russell supra). Vectors containing rep genes and TRs derived from serotype 2 are particularly preferred because serotype 2 vectors have been characterized in great detail and constructs derived from serotype 2 are commonly available. Particular AAV vectors and AAV proteins of different serotypes are discussed in Chao et al., Mol. Ther. 2:619–623, 2000; Davidson et al., Proceedings of the National Academy of Sciences 97:3428–3432, 2000; and Xiao et al., J. Virol. 72:2224–2232, 1998.

Non-Naturally Occurring Nucleic Acids

The invention provides non-naturally occurring nucleic acids having nucleotide sequences encoding AAV Rep and Cap proteins. AAV rep (Rep 40, 52, 68, 78) and cap (VP1, VP2, VP3) genes encode viral proteins that allow replication of the viral genome and packaging of the genome into a virion, respectively. Non-naturally occurring nucleic acids of the invention include a first nucleotide sequence encoding at least one Rep protein and a second nucleotide sequence encoding at least one Cap protein. The first nucleotide sequence can encode one or more Rep proteins (e.g., Rep 40, 52, 68, 78), but preferably encodes Rep proteins 52 and 78 for optimal replication and expression of the non-naturally occurring nucleic acid. The second nucleotide sequence includes a polynucleotide encoding a portion of a Cap protein found in an AAV of a first serotype but not in an AAV of a second serotype (differing from the first serotype) as well as a polynucleotide encoding a portion of a Cap protein found in the AAV of the second serotype but not in the AAV of the first serotype. Using methods of the invention, modified (e.g., chimeric) cap sequences are synthesized that contain polymorphic sequences from AAV serotypes 1 through 8, resulting in a polynucleotide encoding a Cap protein having amino acid sequences from more than one serotype. The first and second nucleotide sequences are typically interposed between two AAV TRs. The rep and cap genes used in compositions and methods of the invention can be naturally- or non-naturally occurring mutant versions of AAV rep and cap genes. Non-naturally occurring nucleic acids are preferably present within a vector (e.g., expression vector, plasmid cloning vector) that allows replication and expression of the non-naturally occurring nucleic acid as well as the transfer of the nucleic acid from one host cell to another.

Figure 4:
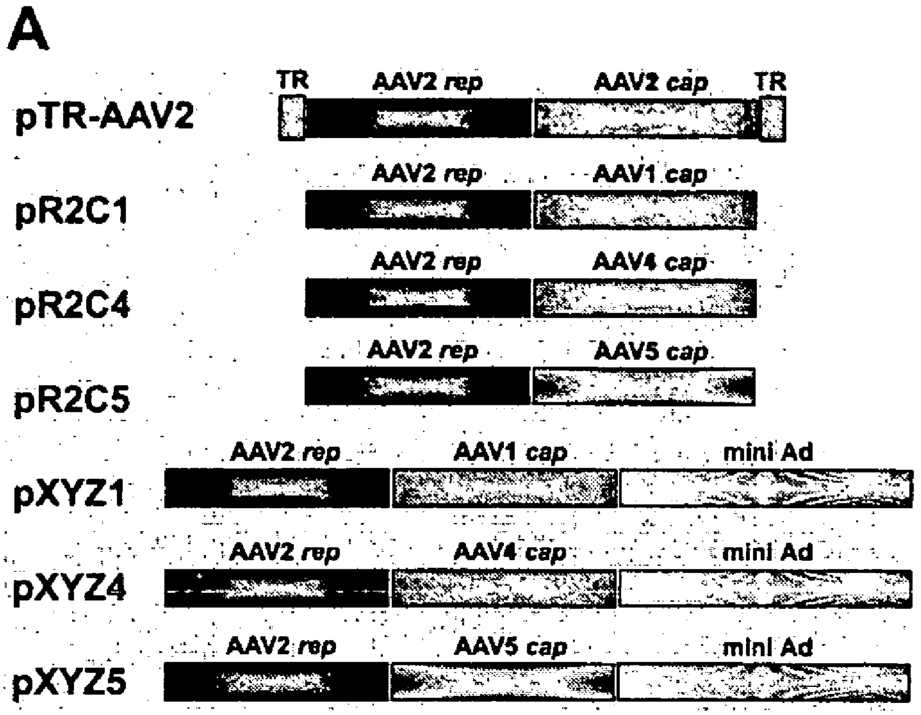
FIG. 4 is a schematic diagram of AAV helper vectors and replication competent transfer vectors. pTR-AAV2 contains a WT AAV2 genome. pR2C1, a pACG2 derivative, is a hybrid helper vector containing an open reading frame (ORF) coding for AAV2 rep genes from the vector linked to the ORF coding for AAV1 cap genes, which was amplified by the PCR-mediated protocol from WT AAV1 DNA. pR2C4 is a similar helper vector linking AAV2 rep gene ORF to AAV4 cap genes (derived from pAAV5-2). pXYZ1, pXYZ4, and pXYZ5 contain rep2cap1, rep2cap4, and rep2cap5 helper cassettes respectively, inserted into a pXYZ background. pXYZ, a mini Ad vector helper containing E2A, E4, and VA genes of Ad type 5 (Ad5), was constructed from pAdEasy.

For use as helper vectors in methods of producing rAAV virions, the non-naturally occurring nucleic acids can further contain a third nucleotide sequence encoding at least one molecule providing helper function. AAV is a helper-dependent parvovirus in that it requires coinfection with another virus (such as Ad or a member of the herpes virus family) to undergo a productive infection in cultured cells. See Ward and Berns, J. Virol., 70:4495, 1996. Helper function may be provided by gene products (e.g., RNA, polypeptides) derived from Ad or a member of the herpes virus family. Ad helper gene products include E1a, E1b, E2a, E4orf6, and VA (Weitzman et al., J. Virol., 70:1845–1854, 1996). Nucleic acids encoding Ad proteins utilized in the present invention may be derived from any of a number of Ad serotypes that facilitate AAV infection. For example, sequences derived from Ad5 can be used. Herpes simplex virus (HSV) helper gene products include UL5, UL8, UL52, UL29, and may be derived from any of a number of HSV strains that facilitate AAV infection (Conway et al., J. Virol., 71:8780–8789, 1997; and Feudner et al., J. Virol. Methods 96:97–105, 2001). The rep and cap genes as well as nucleotide sequences encoding a molecule having helper function utilized in the invention can reside in any known suitable expression plasmid or vector. Examples of suitable expression plasmids include helper plasmids pR2C1, pR2C4, pR2C5, pXYZ1, pXYZ4 or pXYZ5 (See FIG. 4).

Combinatorial Vector And Seed Libraries

The invention also includes combinatorial vector libraries and seed libraries. A combinatorial vector library contains a plurality of vectors, each vector harboring a unique non-naturally occurring nucleic acid of the invention. The vectors of the library contain the first and second nucleotide sequences described above and differ from each other by at least one nucleotide. A vector library may be incorporated into a host cell such as an insect cell. In one example of a vector library expressing degenerate (or otherwise modified) capsid genes, library vectors contain the TR sequences of AAV2 (FIG. 4A, vector pTR-AAV2) and nucleic acids that encode AAV Rep protein and modified Cap protein. Upon transfection of Ad5-infected 293 cells, this vector is capable of rescuing replication-competent WT AAV2. The design of this vector allows substituting degenerate fragments or otherwise modified capsid genes for WT AAV2 capsid gene sequences by simple digest with unique restriction enzymes.

A vector library is useful for generating a corresponding virion (i.e., seed) library, which is a collection of chimeric virions that includes at least a first and a second AAV virion. The first and the second virions include the first and second nucleotide sequences described above which are interposed between a first and a second TR. The second virion has a nucleic acid not included within the first virion. The capsids of the first and second virions are preferably composed of WT Cap proteins. For example, each virion of the seed library is composed of WT Cap proteins yet contains a unique non-naturally occurring nucleic acid encoding a modified (e.g., degenerate) Cap protein. The virions of the seed library can be incorporated within at least one host cell. A host cell is any cell permissive to infection by AAV, and includes insect as well as mammalian cells.

Generating Chimeric Cap Genes

Figure 2:
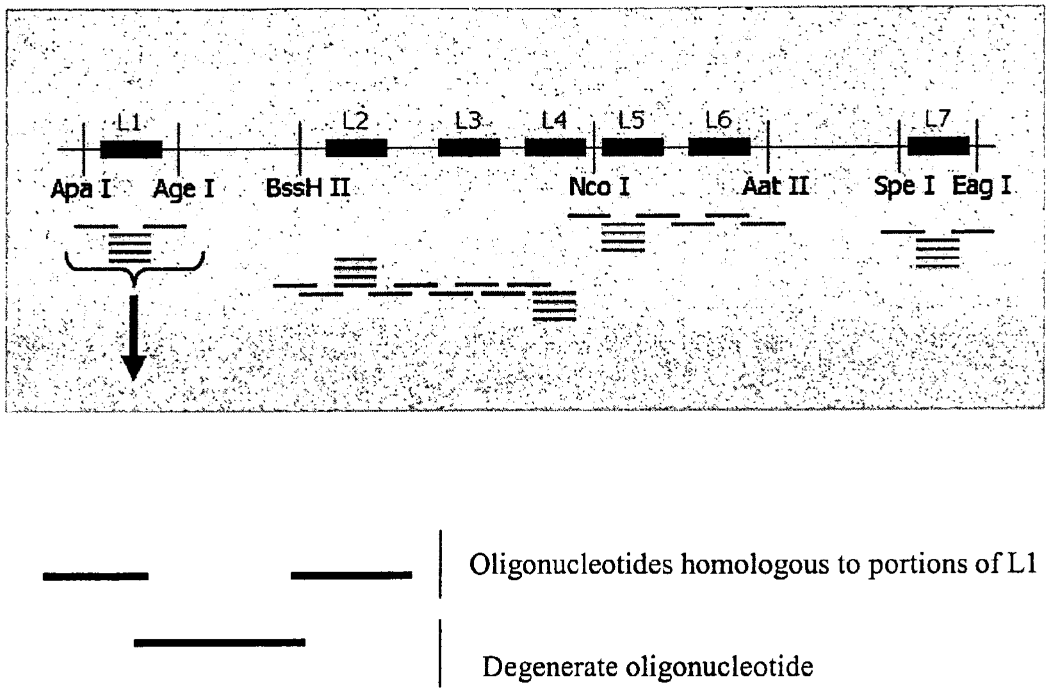
FIG. 2 is a schematic representation of simultaneous modification of seven surface loops within a P1 capsid gene of AAV2.

One aspect of the invention involves the production of AAV cap nucleic acids that are modified, e.g., cap nucleic acids that contain portions of sequences derived from more than one AAV serotype (e.g., AAV serotypes 1–8). Such chimeric nucleic acids can be produced by a number of mutagenesis techniques. A preferred method for generating chimeric cap genes involves the use of degenerate oligonucleotides in an in vitro DNA amplification reaction (FIG. 2). A protocol for incorporating degenerate mutations (e.g., polymorphisms from different AAV serotypes) into a nucleic acid sequence is described in Coco et al. (Nature Biotechnology 20:1246–1250, 2002. In this method, known as degenerate homoduplex recombination, “top-strand” oligonucleotides are constructed that contain polymorphisms (degeneracies) from genes within a gene family. Complementary degeneracies are engineered into multiple bridging “scaffold” oligonucleotides. A single sequence of annealing, gap-filling, and ligation steps results in the production of a library of nucleic acids capturing every possible permutation of the parental polymorphisms.

Any portion of a capsid gene may be mutated using methods such as degenerate homoduplex recombination. Particular capsid gene sequences, however, are preferred. For example, critical residues responsible for binding of an AAV2 capsid to its cell surface receptor heparan sulfate proteoglycan (HSPG) have been mapped. Arginine residues at positions 585 and 588 appear to be critical for binding, as non-conservative mutations within these residues eliminate binding to heparin-agarose. Computer modeling of the AAV2 and AAV4 atomic structures identified seven hypervariable regions that overlap arginine residues 585 and 588, and that are exposed to the surface of the capsid. These hypervariable regions are thought to be exposed as surface loops on the capsid that mediate receptor binding. Therefore, these loops are preferred targets for mutagenesis in methods of producing chimeric virions with tropisms different from WT virions.

Figure 3:
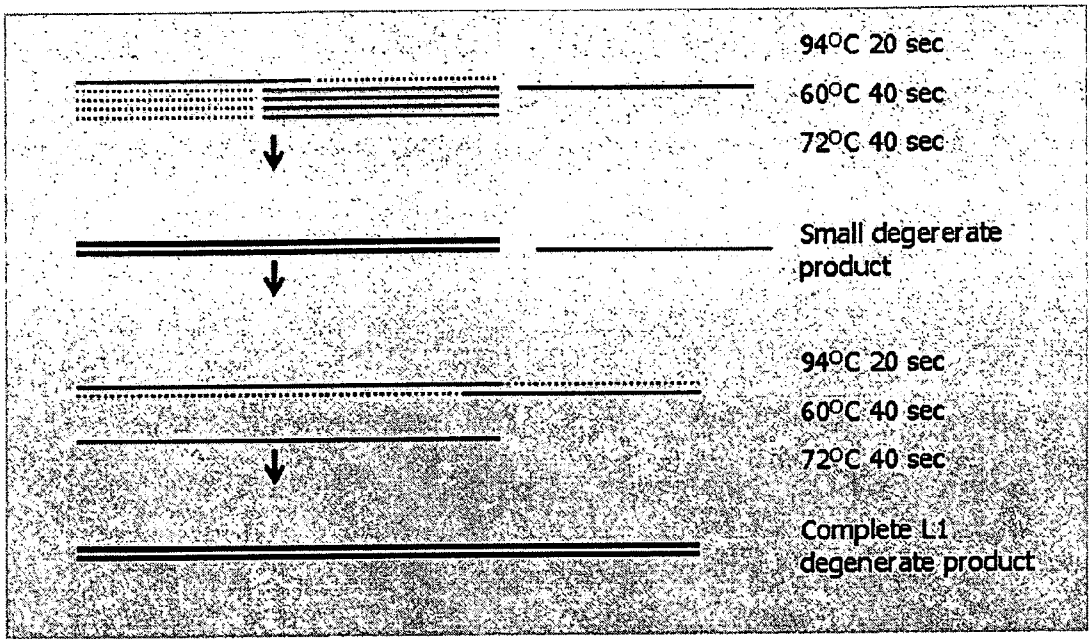
FIG. 3 is a schematic representation of an extension protocol incorporating degenerate oligonucleotides.

In methods of the invention for generating a library of cap genes that contain degeneracies corresponding to every polymorphism within the 7 loops of AAV capsid genes serotypes 1 through 8, the Coco et al. (supra) method is modified to allow the generation of a full-length double-stranded modified fragment. FIG. 3 illustrates the flow of the protocol shown for mutagenizing AAV capsid loops L1 through L7. An L1 fragment containing degeneracies corresponding to polymorphisms within L1 is first generated as shown in FIG. 3. In this protocol, a trio of overlapping oligonucleotides are annealed and extended by a DNA polymerase (e.g., Pfu polymerase). Two of these oligonucleotides are homologous to the WT AAV2 cap sequence to be amplified and are non-contiguous, in that there is a gap between the two oligonucleotides. The third oligonucleotide shares some level of homology to the sequence encompassed by the gap, but includes polymorphisms from other AAV serotypes (e.g., degeneracies). This third oligonucleotide is complementary to and therefore anneals to the ends of the first two oligonucleotides, resulting in a gap in the top strand as well as two over-hangs on the bottom strand. The polymerase fills in the gap and the two overhangs, resulting in a double-stranded extension product. The extension product is purified and annealed to a fourth overlapping oligonucleotide and the extension/purification step is repeated. Fragments incorporating L2–L4, L5–6 and L7 are synthesized in a similar fashion by sequentially adding more overlapping oligonucleotides and purifying the extension product using agarose gel electrophoresis. The final product (fragment incorporating L1–L7) is amplified using PCR and subcloned into a suitable vector (e.g., pTR-AAV2) to generate a vector DNA library containing degenerate VP1 capsid genes.

Another mutagenesis technique that may be used in methods of the invention is DNA shuffling. DNA or gene shuffling involves the creation of random fragments of members of a gene family and their recombination to yield many new combinations. To shuffle AAV capsid genes, several parameters are to be considered, including: involvement of the three capsid proteins VP1, VP2, and VP3 and different degrees of homologies between 8 serotypes. To increase the likelihood of obtaining a viable rcAAV vector with a cell- or tissue-specific tropism, for example, a shuffling protocol yielding a high diversity and large number of permutations is preferred. An example of a DNA shuffling protocol for the generation of chimeric rcAAV is random chimeragenesis on transient templates (RACHITT), Coco et al., Nat. Biotech. 19:354–358, 2001.

RACHITT differs from other DNA-shuffling strategies in that single-stranded (rather than double-stranded) fragments are hybridized onto a full-length single-stranded homologous gene that serves as a scaffold. The scaffold in RACHITT is designed with a number of properties that contribute to a low background of unshuffled parental clones and a high level of diversity amongst recombinants. The resulting fragments are then created and size-fractionated in a manner analogous to previously reported strategies. Stemmer, W. P. C., Nature 270:389–391, 1994; Schmidt-Dannert et al., Nat. Biotech. 18:750–753, 2000; and Oreneis et al., Nat. Struct. Biol. 9:238–242, 2001.

The RACHITT method can be used to recombine two PCR fragments derived from AAV genomes of two different serotypes (e.g., AAV 1 and AAV2). For example, conservative regions of the cap gene, segments that are 85% identical, spanning approximately 1 kbp and including initiating codons for all three genes (VP1, VP2, and VP3) can be shuffled using a RATCHITT or other DNA shuffling protocol, including in vivo shuffling protocols (U.S. Pat. No. 5,093,257; Volkov et al., NAR 27:e18, 1999; and Wang P. L., Dis. Markers 16:3–13, 2000). A resulting combinatorial chimeric library can be cloned into a suitable AAV TR-containing vector (e.g., pTR-AAV2) to replace the respective fragment of the WT AAV genome. Random clones can be sequenced and aligned with parent genomes using AlignX application of Vector NTI 7 Suite Software. From the sequencing and alignment, the number of recombination crossovers per 1 Kbp gene can be determined. Alternatively, the variable domain of AAV genomes can be shuffled using methods of the invention. For example, mutations can be generated within two amino acid clusters (amino acids 509–522 and 561–591) of AAV that likely form a particle surface loop in VP3. To shuffle this low homology domain, recombination protocols can be utilized that are independent of parent's homology (Ostermeier et al., Nat. Biotechnol. 17:1205–1209, 1999; Lutz et al., Proceedings of the National Academy of Sciences 98:11248–11253, 2001; and Lutz et al., NAR 29:E16, 2001) or a RACHITT protocol modified to anneal and recombine DNA fragments of low homology.

Combinatorial libraries can also be constructed using insertions of short randomized oligonucleotides into certain positions of capsid genes that likely form a loop and are exposed at a particle surface to interact with a cell surface receptor (e.g., amino acids 509–522 and 561–591 in AAV2) (Xie et al, Proceedings of the National Academy of Sciences, v. 99;10405–10410, 2002). Such libraries can be used to select for virions with new cell/tissue tropisms. Selection of virions involves the protocol described in FIGS. 1B and 1C.

Methods of making AAV capsid mutants in addition to degenerate oligonucleotide synthesis, random peptide insertion, and RATCHITT methods might also be used. Examples of alternative methods include site-directed mutagenesis (Wu et al., J. Virol. 72:5919–5926); molecular breeding, nucleic acid, exon, and DNA family shuffling (Soong et al., Nat. Genet. 25:436–439, 2000; Coco et al., Nature Biotech. 2001; 19:354; and U.S. Pat. Nos. 5,837,458; 5,811,238; and 6,180,406; Kolkman and Stemmer, Nat. Biotech. 19:423–428, 2001; Fisch et al., Proceedings of the National Academy of Sciences 93:7761–7766, 1996; Christians et al., Nat. Biotech. 17:259–264, 1999); ligand insertions (Girod et al. Nat. Med. 9:1052–1056, 1999); and cassette mutagenesis (Rueda et al. Virology 263:89–99, 1999; Boyer et al., J. Virol. 66:1031–1039, 1992). For mutational analyses of the AAV capsid gene, see Wu et al., J. Virol. 74:8635–8647, 2000 and Rabinowitz et al., Virology 265;274–285, 1999.

Constructing a Vector Library

Methods of constructing a vector library of the invention involve several steps. The first step of the method involves providing a first and a second polynucleotide. The first and second polynucleotides feature an identical nucleotide sequence encoding an AAV Cap protein. In a second step of the method, these polynucleotides are mutated, resulting in a plurality of Cap-encoding mutants. The polynucleotides are mutated using any of a number of the techniques described above for mutating cap sequences. Each mutant includes 1) a nucleotide sequence that encodes a portion of a Cap protein found in an AAV of a first serotype but not in an AAV of a second serotype (differing from the first serotype), and 2) a polynucleotide encoding a portion of a Cap protein found in the AAV of the second serotype but not in the AAV of the first serotype. In a third step of the method, each mutant is placed into a vector, preferably an expression vector that also encodes at least one Rep protein. The resultant collection of vectors expressing chimeric Cap proteins is a combinatorial vector library of the invention which is used for generating a seed library.

Constructing A Seed Library

To generate a seed library, the vector library is introduced into a host cell. Rep and Cap gene products having WT Rep and Cap function are provided to the cell. Any host cell permissive to AAV growth might be used. However, host cells that silence AAV promoters and therefore prevent expression of the modified cap genes are preferred. For example, insect cells (e.g., Sf9 cells) might be used. Although Rep and Cap gene products may be provided using any suitable means, a preferred method involves the use of recombinant baculoviruses. For example, insect cells are coinfected with baculoviruses RepBac and VPBac, expressing Rep and Cap, respectively, at an MOI of 5 each. For methods of using insect cells as AAV-producing cells, see Urabe et al., Human Gene Therapy 13:1935–1943, 2002. The cells are cultured under conditions that allow production of virions (see U.S. Pat. No. 6,146,874). In the presence of the Rep and Cap gene products, the vectors of the library are replicated and packaged into capsids, resulting in a first population of virions referred to as a seed library. These virions are composed of WT AAV2 Cap proteins and each contains a unique vector of the vector library. At a suitable time post-infection (e.g., 60 hours), the resultant virions are harvested from the cells. The production of rcAAV can be accomplished by any known suitable method in addition to those described herein. See, e.g., U.S. patent application Ser. No. 09/746,246; U.S. Pat. No. 5,968,750; and He et al., Proceedings of the National Academy of Sciences 95:2509–2514, 1998.

In one example of constructing a seed library employing a baculovirus system that involves insect cells as host cells, a vector library is transfected into an insect cell line. Insect cells suitable as host cells for the production of rAAV and rcAAV include Sf9 and Sf24 cells (Urabe et al., Human Gene Therapy 13:1935–1943, 2002). The Sf9 cell line is a clonal isolate derived from the parental *Spodoptera frugiperda* cell line IPLB-Sf-21-AE. Cell transfection techniques are widely known in the art and include lipid-mediated protocols (e.g., lipofection). For example, lipofection protocols are discussed in Katsel et al., Biotechnol. Annu. Rev. 5:197–220, 2000.

The cells are then infected with two recombinant baculoviruses: RepBac (baculovirus encoding AAV2 Rep proteins) and VPBac (baculovirus encoding WT Cap proteins) at an MOI of 5 each (FIG. 1B). The heterologous system of insect cells is utilized in order to attenuate the expression from the P40 promoter controlling shuffled capsid genes, since WT AAV2 promoters are either silent or very inefficient in insect cells. In contrast, baculovirus promoters, driving the expression of rep and cap genes in recombinant helper vectors RepBac and VPBac are fully functional and provide in trans the products of these genes at an appropriate stoichiometry.

This arrangement provides rescuing, replication and pseudo-packaging of shuffled (or otherwise modified), chimeric genomes into AAV2 capsids. The Sf9 cells, grown in suspension culture, are co-infected with these two viruses and three days later, virions containing chimeric rcAAV vectors are recovered. The recovered virions are composed of an rcAAV vector encoding a shuffled (or otherwise modified) Cap protein and a capsid containing WT Cap protein. This seed library (FIG. 1B) is subsequently purified using iodixanol gradient centrifugation followed by heparin affinity chromatography. Such a purified library is titered for physical as well as infectious virions using standard techniques.

The virions produced in Sf9 cells are indistinguishable from 293 cell-produced rAAV based on physical properties and biological activities. The yield of vector (genome)-containing particles produced per Sf9 cell approaches $5\times10^4$, which is about one log higher compared to a standard co-transfection protocol. The high yield per cell basis derives from the engineering of the helper baculovirus vectors based on the use of strong and weak baculovirus promoters to deliver an appropriate stoichiometry of Rep52 and 78 proteins, as well as VP1, VP2, and VP3 capsid proteins of AAV2.

Master Library

The seed library generated above is used to generate a second population of virions that are collectively referred to as a master library. This library contains at least a first and a second AAV virion, each virion including: 1) a nucleic acid including first and second nucleotide sequences encoding Rep and modified Cap, respectively, 2) a first and a second TR, between which the first and second nucleotide sequences are interposed, and 3) at least one AAV Cap protein encoded by the second nucleotide sequence. The second virion includes a Cap protein not included within the first virion. Like the seed library virions, the master library virions contain a vector of the seed library and therefore a modified (e.g., degenerate) cap gene. However, unlike the seed library virions, the master library virions are composed of modified (e.g., degenerate) Cap proteins encoded by the vector they contain within. The virions of the master library may be incorporated into a host cell, such as a mammalian cell (e.g., 293 cells).

Construction of a Master Library

To generate a master library, a suitable host cell is infected with the first population of virions (i.e., seed library) under conditions that allow for the production of virions. Suitable host cells are those that are permissive to both an AAV infection and helper virus (e.g., Ad) infection. Examples of suitable host cells include 293, HeLa, Cos, U87, KB, HepG2, and Vero cells. The host cell is infected with the seed library at an effective (e.g., 0.02, 0.05, 0.1, 0.2, 0.3) MOI to ensure that most of the cells are infected with a single rcAAV virion. An effective MOI results in most of the cells being infected with a single virion containing a chimeric rcAAV vector. For example, 293 cells can be infected with a seed library at a low MOI of 0.1 (FIG. 1C). The cells are also infected with a helper virus such as Ad at a suitable MOI (e.g., MOI of 1, 2, 3, 4, 5, 6, 7, 8, 9, 10) to provide helper functions. As a result of a productive infectious cycle, every cell infected with a virion containing a chimeric rcAAV vector will produce a population of the unique rAAV vectors as well as capsids encoded by this single degenerate member. Once the cells have been cultured for a duration of time that permits a productive infectious cycle (e.g., about 60 hours), the cells are harvested. Virions are then purified from the cells using a suitable purification technique. An example of a suitable purification protocol is centrifugation in an iodixanol gradient. See Gao et al., Hum. Gene Ther. 9:2353–2362, 1998; U.S. Pat. No. 6,146,874; and Zolotukhin et al., Gene Ther. 6:973–985, 1999.

Although rAAV vectors can be propagated in a manner similar to that of WT AAV2 (up to $10^5$–$10^6$ genomes per infected cell), the actual amplification factor will depend on a viability index of a particular combinatorial library. Not all degenerate cap genes will produce packagable virions and this index will depend on a particular mutagenesis strategy. The first selection criteria for the master library, therefore, will be an ability of degenerate capsid genes to produce viable virions in 293 cells. A physical titer of the master library can be determined using a technique such as a standard dot-blot assay. In addition, helper virus (e.g., Ad5) contamination is titered by a standard plaque assay.

Selecting for Cell- or Tissue-Specific Virions

The master library can be used to select virions having chimeric capsids (e.g., capsids containing a degenerate or otherwise modified Cap protein) that are targeted to particular cell and tissue types. For example, virions made according to the invention include those that exhibit a new tropism, e.g., those capable of infecting cells normally non-permissive to AAV infection, as well as those that exhibit an increased or decreased ability to infect a particular cell or tissue type. As another example, virions made according to the invention include those that lack the ability to infect cells normally permissive to AAV infection. To select for virions having a particular cell- or tissue-specific tropism, the second population of virions (i.e., master library) is introduced into a target cell. Preferably, the target cell is also infected with a helper virus (e.g., Ad). The target cell is cultured under conditions that allow the production of virions, resulting in a third population of virions that are harvested from the target cell. This third population of virions has been selected for having a tropism for that target cell.

As controls in a typical experiment in which virions having a particular tropism are selected, cells in different flasks or dishes can be simultaneously infected with WT AAV or rAAV using the same conditions as used for the library. Several hours post-infection, cells can be harvested, washed and the virions purified using a suitable purification method (See Gao et al., Hum. Gene Ther. 9:2353–2362, 1998; U.S. Pat. No. 6,146,874; and Zolotukhin et al., Gene Ther. 6:973–985, 1999). AAV and helper virions (e.g., Ad) from each infection can be titered, by real-time PCR for example, and the AAV virions can then be further propagated, resulting in a stock of selected virions.

Once the third population of virions having a desired tropism is isolated, nucleic acid from the virions is isolated. The sequence of the nucleotide sequence encoding the at least one AAV Cap protein is determined (e.g., by DNA sequencing and restriction analysis). Virions made and selected according to the invention that can specifically target diseased cells or tissues over non-diseased cells or tissues are useful. For studies involving virions with altered tropisms or cell specificities, see Soong et al., Nat. Genet. 25:436–439, 2000; and U.S. Pat. No. 6,180,406.

Construction of Helper Plasmids

Based on virions generated in the combinatorial master library and selected for a cell- or tissue-specific tropism, helper vectors encoding degenerate (or otherwise modified) capsid proteins with particular tropisms can be generated. A method of generating a helper vector according to the invention involves placing the isolated nucleotide sequence encoding the at least one AAV Cap protein into a second vector. This second vector, i.e., a helper vector, introduces at least one modified AAV cap gene to the host cell. Expression of AAV cap from the helper vector results in the production of rAAV capsids. For example, a helper plasmid encoding a degenerate Cap protein can be used to produce virions that are cell- or tissue-specific. In addition to at least one cap gene, helper plasmids of the invention can contain a nucleotide sequence encoding AAV Rep protein. A combinatorial library of virions composed of chimeric capsids and chimeric rcAAV vectors provides a diverse array of virions that are cell- or tissue-specific. These virions, however, contain nucleic acids encoding AAV WT Rep and modified Cap proteins. Virions that can be used in a gene therapy application, for example, encode a therapeutic or marker protein, rather than AAV proteins. To produce a cell- or tissue-specific virion that contains a chimeric capsid (e.g., capsid containing a degenerate or otherwise modified Cap protein) and a nucleic acid encoding a therapeutic or marker protein, a helper vector that encodes the selected degenerate (or otherwise modified) cap gene is constructed.

To generate helper vectors that can be used to propagate virions that are cell- or tissue-specific, several steps are followed. Upon several rounds of reiterative selection, virions composed of chimeric capsids (e.g., capsids containing a degenerate or otherwise modified Cap protein) and chimeric rcAAV vectors are propagated that are capable of establishing a productive infection in otherwise non-permissive cell lines, for example. From these cells, viral DNA is purified and the chimeric (e.g., degenerate or otherwise modified) portion of the genome is amplified and cloned using PCR-mediated protocols. Sequencing and restriction analysis determines the complexity of the selected population. The major species are subcloned into TR-less plasmid backbones to produce a helper similar to pACG2r1c, or pACG2r5c (see FIG. 4). Examples of helper vectors that can be used to propagate virions composed of chimeric capsids (e.g., capsids containing a degenerate or otherwise modified Cap protein) and rAAV vectors include expression vectors that contain degenerate or otherwise modified) cap genes derived from one or more AAV serotypes (e.g., 1, 2, 3, 4, 5, 6, 7, and 8).

Helper vectors of the invention are used to pseudotype rAAV (e.g., rAAV2) vectors, resulting in virions that feature newly acquired tropisms to particular cell lines. The helper vectors of the invention can also be used to pseudotype rAAV vectors of any serotype, including serotypes 1, 3, 4, 5, 6, 7, and 8. Alternatively, virions with enhanced tropisms to known, previously characterized cell surface markers can also be used to generate helper vectors. As an example of such a selection, a virion having a tropism to cells expressing the human long-form leptin receptor (Ob-$R_L$) can be selected and used to construct a helper vector encoding Cap proteins that confer the viral tropism to these cells. White et al., Diabetes 49:1443–1450, 2000.

Once a helper vector is generated, it may be used to propagate a rAAV having a desired tropism. Typically the rAAV contains a non-AAV nucleic acid (e.g., encoding a therapeutic or marker molecule) and does not contain rep or cap sequences. In a method of propagating a rAAV containing a non-AAV nucleic acid, the following components are provided to a host cell: 1) the helper vector, 2) a nucleotide sequence encoding at least one AAV Rep protein, 3) at least one molecule having helper function (e.g., Ad or herpesvirus helper function), and 4) a nucleic acid including two AAV TRs and a non-AAV nucleic acid interposed between the TRs. The host cell is cultured under conditions that allow the production of virions and the resultant virions are harvested from the cell. These virions contain the nucleic acid of 4) and a capsid composed of Cap proteins encoded by the nucleotide sequence of 3). The non-AAV nucleic acid may encode any therapeutic or marker molecule (e.g., RNA, polypeptide). The helper vector can further include a nucleotide sequence encoding at least one AAV Rep protein, thereby providing both rep and cap gene products from the same vector. The host cell can be any cell permissive to infection by rAAV and helper virus (e.g., Ad), including mammalian cells such as human cells.

rAAV Vectors

The invention provides methods for producing stocks of virions composed of chimeric capsids (e.g., capsids containing degenerate, shuffled or otherwise modified Cap protein) and vectors having a non-AAV nucleotide sequence (e.g., rAAV vectors). An rAAV vector used or made by methods of the invention is a nucleic acid sequence that includes at least those AAV sequences required in cis for replication and packaging (e.g., functional TRs) of the virus.

In some applications including gene therapy applications, rAAV vectors contain a non-AAV nucleic acid. Non-AAV nucleic acids include, for example, marker or reporter genes (e.g., a nucleic acid encoding green fluorescent protein). Non-AAV nucleic acids also include therapeutic genes (e.g., a leptin gene). Examples of therapeutic genes encoded by rAAV vectors include CFTR gene for treating cystic fibrosis (Flotte et al., Chest 120:124S–131S, 2001), factors IX and VIII for treating hemophilia (Walsh et al., Haemophilia Suppl. 2:60–67, 2002), and FasL, Bcl-2, IL-4, and IL-10 for treating diabetes (Kapturczak et al., Curr. Mol. Med. 1:245–258, 2001). Examples of useful rAAV vectors are those that have one or more AAV WT genes deleted in whole or in part, but retain functional flanking TR sequences. rAAV vectors can be derived from any AAV serotype, including 1, 2, 3, 4, 5, 6, 7, and 8. Preferred rAAV vectors used in the invention are constructed using plasmid pTR-UF (Klein et al., Exp. Neurol. 150:183–194, 1998; and Zolotukhin et al., J. Virol. 70:4646–4654, 1996) and contain AAV2 TRs. For example, a particularly preferred vector of the invention is an AAV2 vector pseudotyped with a chimeric capsid derived from degenerate capsid genes of both AAV serotype 2 and at least one AAV serotype other than 2, e.g., AAV1, AAV3, AAV4, AAV5, AAV6, AAV7, and AAV8 capsids.

Expression Control Sequences

The nucleic acids of the invention can include one or more expression control sequences operatively linked to the non-AAV nucleic acid. Numerous such sequences are known. Those to be included in the nucleic acids of the invention can be selected based on their known function in other applications. Examples of expression control sequences include promoters, insulators, silencers, IRESs, enhancers, initiation sites, termination signals, and polyA tails.

To achieve appropriate levels of molecules (e.g., polypeptides, RNAs) encoded by a non-AAV nucleic acid (e.g., therapeutic protein) in a host cell, any of a number of promoters suitable for use in the selected host cell may be employed. For example, constitutive promoters of different strengths can be used to express molecules (e.g., polypeptides, RNAs) encoded by non-AAV nucleic acids (e.g., therapeutic proteins).

Expression vectors in accordance with the present invention may include one or more constitutive promoters, such as viral promoters or promoters from mammalian genes that are generally active in promoting transcription. Examples of constitutive viral promoters include the Herpes Simplex virus (HSV), thymidine kinase (TK), Rous Sarcoma Virus (RSV), Simian Virus 40 (SV40), Mouse Mammary Tumor Virus (MMTV), Ad E1A and CMV promoters. Examples of constitutive mammalian promoters include various housekeeping gene promoters, e.g., the chicken β-actin promoter.

Inducible promoters and/or regulatory elements may also be contemplated for use with the nucleic acids of the invention. Examples of suitable inducible promoters include promoters from genes such as cytochrome P450 genes, heat shock protein genes, metallothionein genes, and hormone-inducible genes, such as the estrogen gene promoter. Another example of an inducible promoter is the tetVP16 promoter that is responsive to tetracycline. The sterol regulatory-binding protein (SREBP-1c) promoter is another inducible promoter useful within the invention (Deng et al., Biochem. Biphys. Res. Commun 290:256–262, 2002; Kim et al., J. Clin. Invest. 101:1–9, 1998; and Azzout-Marniche et al., Biochem. J. 350 Pt 2:389–393, 2000).

Tissue-specific promoters and/or regulatory elements are useful in certain embodiments of the invention. Examples of such promoters that may be used with the expression vectors of the invention include promoters from the transphyretin, α1-antitrypsin, plasminogen activator inhibitor type 1 (PAI-1), albumin, hepatitis B virus core protein, apolipoprotein AI and LDL receptor genes, specific for liver cells; MLC-2v, alpha myosin heavy chain, and myosin light chain-2 genes, specific for cardiac cells; and the utrophin promoter A, human dystrophin, creatine kinase, myogenin, alpha myosin heavy chain, and natriuretic peptide muscle specific promoters, specific for muscle cells.

AAV Mutants

Using the above-described methods, virions having chimeric capsids (e.g., capsids containing a degenerate or otherwise modified Cap protein) can be made. To further alter the capsids of such virions, e.g., to enhance or modify the binding affinity for a specific cell type, additional mutations can be introduced into the capsid of the virion. For example, suitable chimeric capsids may have ligand insertion mutations for facilitating viral targeting to specific cell types. The construction and characterization of AAV capsid mutants including insertion mutants, alanine screening mutants, and epitope tag mutants is described in Wu et al., J. Virol. 74:8635–45, 2000. Methods of making AAV capsid mutants are known, and include site-directed mutagenesis (Wu et al., J. Virol. 72:5919–5926); molecular breeding, nucleic acid, exon, and DNA family shuffling (Soong et al., Nat. Genet. 25:436–439, 2000; Coco et al., Nature Biotech. 2001; 19:354; and U.S. Pat. Nos. 5,837,458; 5,811,238; and 6,180,406; Kolkman and Stemmer, Nat. Biotech. 19:423–428, 2001; Fisch et al., Proceedings of the National Academy of Sciences 93:7761–7766, 1996; Christians et al., Nat. Biotech. 17:259–264, 1999); ligand insertions (Girod et al. Nat. Med. 9:1052–1056, 1999); cassette mutagenesis (Rueda et al. Virology 263:89–99, 1999; Boyer et al., J. Virol. 66:1031–1039, 1992); and the insertion of short random oligonucleotide sequences.

EXAMPLES

The present invention is further illustrated by the following specific examples. The examples are provided for illustration only and are not to be construed as limiting the scope or content of the invention in any way.

Example 1

Building Combinatorial Viral Libraries

To build a combinatorial library, insect cells are employed. Transfection of an Sf9 insect cell line with plasmid DNA using commercially available liposomes routinely reaches 10% of the total cell population yielding about $10^6$ rAAV2-GFP infectious virions/ug of transfected plasmid. At such efficiency, $10^6$ cells (10% of $10^7$ of total number of cells) can be transfected in one T75 flask using only 10 μg of plasmid DNA. This produces $10^7$ infectious viral particles, which sets the upper limit for the complexity of a seed library. Even though this protocol delivers a reasonably high complexity, the possibility that other conditions can further improve the transfection efficiency and final diversity are investigated. For example, in order to further improve the transfection efficiency of Sf9 cells, the plasmid DNA is treated with *E. coli* DNA gyrase (TopoGen, Columbus, Ohio). In a pilot experiment a Form I TR-containing plasmid DNA pFBGR (Urabe et al., Nature Biotechnology in press, 2002) is converted into Form II by digesting DNA with restriction endonuclease generating a unique cut (e.g. XhoI). Subsequent gel purification of linear form and ligation produces a Form I DNA. Half of such DNA is treated with DNA gyrase as specified by the vendor. Upon purification, un-treated and treated plasmids, along with CsCl-grade positive control plasmid DNA, are transfected into Sf9 cells. The Sf9 cells are co-infected with RepBac and VPBac (MOI of 5 each). Three days post-transfection rAAV-GFP are harvested and titered using a standard ICA assay (Zolotukhin et al., Gene Ther 6: 973–985, 1999).

Once the viability index of clones derived from the original experiment is determined, the ligation of the shuffled DNA and recipient vector pTR-AAV2 is scaled up to derive 10 μg of DNA total. This plasmid (treatment with DNA gyrase is optional) is transfected into adherent Sf9 cells ($10^7$ cells grown in T75 flask). Cells are co-infected with RepBac and VPBac (MOI of 5 each). rcAAV virions are harvested 72 hr post-transfection and purified using a 10-fold scale-down standard protocol of iodixanol gradient centrifugation followed by heparin affinity chromatography (Zolotukhin et al., Gene Ther. 6:973–985, 1999). Purified rcAAV virions are titered using real-time PCR assay and ICA (Potter et al., Methods Enzymol in press, 2002). These titers provide important information regarding particles/infectivity ratio of the purified stock. This viral stock represents a seed library.

The next step of the protocol is the production of a master library, i.e., a library of rAAV shuffled genomes packaged into the cognate capsids. To produce such a library HEK 293 cells are infected with seed viral stock at an MOI of 0.1. Cells are also co-infected with Ad5 helper (MOI of 5). Using such a low MOI for rAAV requires high efficiency infection protocols to be employed in order not to decrease the final viral titer/library complexity. Since tripeptydil aldehyde proteasome inhibitors enhance the transduction efficiencies of rAAV-pseudotyped vectors, these reagents are tested for the next step of master library production. Specifically, $10^5$ of 293 cells in a 60 mm dish are pre-treated with 40 μM of the proteasome inhibitor LLnL (N-acetyl-L-leucinyl-L-leucinyl-norleucinal 1 h prior to infection exactly as described (Potter et al., Methods Enzymol. in press, 2002), and the inhibitor is retained in the medium throughout the 24-h infection. Cells are infected with $10^4$ infectious viral particles from the seed library and co-infected with AdS (MOI of 5). At 48 h post-infection cells are harvested and virions are purified using centrifugation in an iodixanol gradient. Purified vector stocks from LLnL-treated and un-treated cell preparations are titered using a real-time PCR assay.

Once the optimal conditions for the master library are refined, a large scale library is generated by infecting $10^8$ or more 293 cells, with or without LLnL inhibitor. The resulting library is purified and titered as described above. Since not all shuffled genes produce viable virions (a viability index is determined), this step selects for packageable capsids only. The final titer of the master library is expected to be no less than $10^9$ physical DNAseI-resistant particles (drp). In addition, Ad5 contamination is titered by a standard plaque assay. Ad5 titer is reduced by more than two logs after separation of rAAV and Ad in iodixanol gradient and is anticipated to be about $10^8$ plaque-forming units (pfu). The infectious titer of virions in the library is determined in each particular case at the next stage of selection using specific established or primary cell lines.

Example 2

Analysis of Capsid Gene Homologies of AAV Serotypes 1 Through 5

In order to develop a viable shuffling strategy, homologies of the respective capsid genes of AAV1–5 were analyzed using AlignX application of the Vector NTI 7 Suite software (InforMax, Inc, Bethesda Md.). A multiple alignment showed that the homologies of capsid genes and proteins were not distributed across the length in a regular fashion. For example, regions containing start codons were considerably less divergent as compared to regions within VP3 (variable domain, Rabinowitz et al., Virology 278:301–308, 2000). The degree of homology/divergence imposes practical considerations on the strategy of library construction. For example, it is technically more feasible to start shuffling DNA species with higher homologies (e.g. closely related serotypes AAV2 and AAV3, or AAV1 and AAV2, Table. 1). At a later stage of shuffling, it is possible to incorporate into the breeding mix more distant relatives and fine-tune the annealing conditions respectively. In addition, within the whole length of the capsid gene of 2.2 Kbp, the region encoding a variable domain (nt residues 1330–1850) is extremely divergent requiring special shuffling protocols that do not rely on homology between parent genomes (Ostermeier et al., Nat. Biotechnol. 17:1205–1209, 1999; Lutz et al., Proceedings of the National Academy of Sciences 98:11248–11253, 2001; and Lutz et al., Nucleic Acids Research, 29:E17, 2001). In this regard it is helpful to take into account phylogenetic relationship between parents, perhaps applying a "reverse evolution" approach to breed close relatives first. A phylogenetic tree that was developed is similar but not identical to the human parvoviruses evolutionary dendrogram obtained by V. Lukashov and J. Goudsmit (Lukashov et al., J. Virol. 75:2729–2740, 2001). It is worth noting that within the node, branching orders of viruses, e.g. AAV1, AAV2, and AAV3, varied with the genetic region analyzed, and, perhaps, depends on the computational tool utilized.

Example 3

RACHITT-mediated Shuffling of Capsid Genes of AAV Types 1 and 2

A library of plasmid DNAs containing AAV1 and AAV2 shuffled capsid genes was constructed. Sequencing of 6 library clones supported the notion that RACHITT is an efficacious protocol of generating highly mosaic shuffled genes. Conservative regions of the AAV cap gene have been shuffled, spanning about 1 Kbp and including initiating codons for all three genes (from SwaI@2194 to BsiWI@3256 in AAV2 genome, the fragment encodes a peptide from Met1 to Leu350 of VP1). These segments of the respective cap genes are 85% identical. The RACHITT method was used to recombine two PCR fragments derived from AAV1 and AAV2 genomes respectively. The resulting chimeric library was cloned into pTR-AAV2 plasmid vector replacing the respective fragment of WT AAV2. Six random clones were sequenced and aligned with parent genomes using Aligrix application of Vector NTI 7 Suite software. The clones contained an average of 10.5 recombination crossovers per 1 Kbp gene. In addition, no unshuffled parental clones or duplicate occurrences ("siblings") were found among analyzed clones. The results obtained clearly demonstrated the capability of performing shuffling protocols of higher homology donor templates.

Example 4

Production of Purified rAAV WT and Pseudotyped Vectors

Substantial variations in target cell tropism were observed among different AAV serotypes. To investigate and exploit potentials of such diversity, methods to produce and purify both "true type" and pseudotyped virions of serotypes 1, 2, 4, and 5 were developed. "True type" virions are those containing an AAV nucleic acid and an AAV capsid of the same serotype. A Baculovirus system was used to produce rAAV2. This system utilized Sf9 insect cells co-infected with two recombinant baculoviruses. Sf9 cells were infected with viral stocks from 6 individual VPBac plaque isolates. Two days post-infection cells were harvested and lysates were separated using PAAG/SDS electrophoresis, blotted and hybridized with B1 antibodies. Lysate of 293 cells transfected with pACG2 was used as a positive control. The Western blot showed similar stoichiometry of capsid proteins isolated from Sf9 cells and human 293 cells. The heterologous system of insect cells was utilized in order to attenuate expression from the P40 promoter controlling shuffled capsid genes, thereby enabling pseudopackaging of shuffled genomes into AAV2 capsids.

Example 5

Peptide Insertion Libraries

A random peptide epitope display approach was used to modify AAV capsid genes, resulting in diverse libraries of multiple recombinants from which vectors with desired tropisms can be selected. Six separate vector libraries derived from the insertions of either completely random or pre-screened motifs targeted to specific tissues of a human patient were generated.

AAV2 uses HSPG as its primary cellular receptor. In order to identify amino acids within the capsid of AAV2 that contribute to HSPG association, biochemical information about heparin/heparin sulfate (HS), AAV serotype protein sequence alignments, and data from previous capsid studies to select residues for mutagenesis were used. Charged-to-alanine substitution mutagenesis was performed on individual and combinations of basic residues for the production and purification of recombinant viruses that contained a GFP reporter gene cassette. Intact capsids were assayed for their ability to bind to heparin/agarose in vitro and virions that packaged DNA were assayed for their ability to transduce normally permissive cell lines. Critical residues responsible for the binding of AAV capsid to HSPG were determined. Non-conservative mutation of arginine residues at positions 585 and 588 to alanine, alone or in combination, eliminated binding to heparan. Mutation of residues 484, 487, and 532 showed partial binding to heparin-agarose. A general correlation between heparin-agarose binding and infectivity was observed, measured by GFP transduction potential. However, a subset of mutants that partially bound heparin-agarose (R484A and K532A) were completely non-infectious, suggesting that they had additional blocks to infectivity that were unrelated to heparin binding. Conservative mutation of positions 585 and 588 to lysine slightly reduced heparin-agarose binding, and had comparable effects on infectivity. Substitution of AAV2 residues 585 through 590 into a location predicted to be structurally equivalent in AAV5 generated a hybrid virus that bound to heparin-agarose efficiently, was able to package DNA, but was non-infectious. Taken together, these results suggest that R585 and R588 are primarily responsible for HSPG binding and mutation of these residues has little effect on other aspects of the viral life cycle. Computer modeling using the AAV2 VP3 atomic coordinates revealed that residues, which contribute to heparin binding, form a cluster of five basic amino acids on the surface left side of each three-fold axis of symmetry related spike. By substituting random peptide epitopes for a stretch of residues from R585 to A590, the packaging properties of AAV2 capsid were preserved, binding to a native HSPG was eliminated, and a combinatorial library of capsid surface peptide epitopes with a complexity of up to $10^8$ was generated.

To construct vector libraries expressing modified capsid genes, a vector encoding WT Rep and mutant Cap genes placed within WT TR sequences of AA2 was used. Upon transfection of Ad5-infected 293 cells, this plasmid is capable of rescuing replication competent AAV2 defective for binding to HSPG receptor. The design of this vector allows substituting combinatorial epitope display motifs for the segment of WT AAV2 capsid gene encoding residues R585 to A590. This plasmid, designated pTR-AAV2-HSPG (–), was used to insert short oligonucleotide sequences coding for the following peptide motifs:; NNLSPNN (SEQ ID NO:1); NNLLVNN (SEQ ID NO:2); NNEGGNN (SEQ ID NO:3); NNLVSNN (SEQ ID NO:4) (skeletal muscle pre-screened); NNTGGENN (SEQ ID NO:5) (octa-peptide, adipose tissue pre-screened (1)); and NNNNNNN (SEQ ID NO:6) (random).

To construct seed libraries, six 10-cm plates of insect cell line Sf9 (2×107 cells per plate) were transfected each with 10 μg of vector DNA library using lipofection (TransIT-Insecta Transfection ReagentMirus Corporation, Madison, Wis.). Cells were then co-infected with two recombinant baculoviruses, RepBac and VPBac, at an MOI of 5 each. All vector particles of seed libraries have identical AAV2 capsids. Each particle, however, harbors a permutated modified capsid gene. To construct libraries with modified capsids (i.e., master library), 293 cells were infected with the seed libraries at a low MOI of 0.1. The low MOI ensured that most of the cells were infected with a single rcAAV particle. In addition, cells were co-infected with AdS (MOI of 5) to provide helper functions. As a result of a productive infectious cycle, every rcAAV-infected cell produced unique genomes and capsids encoded by this single modified member. Master libraries were purified using iodixanol gradient centrifugation and consisted of modified virions encapsulating cognate modified capsid genes. Upon purification, libraries were titered using dot-blot assay. Table 1 illustrates the titers of the viral stocks.

TABLE I

| | Seed stock titer (drp/ml) | Master stock titer (drp/ml) |
|---|---|---|
| LSP (library #1) | $3.1 \times 10^{10}$ | $1.57 \times 10^{11}$ |
| LLV (library #2) | $2.3 \times 10^{10}$ | $1.74 \times 10^{11}$ |
| EGG (library #3) | $1.8 \times 10^{10}$ | $1.7 \times 10^{11}$ |
| LVS (library #4) | $2.3 \times 10^{10}$ | $4.11 \times 10^{10}$ |
| TGGE (SEQ ID NO: 7) (library #5) | $3.1 \times 10^{10}$ | $5.84 \times 10^{10}$ |
| NNN (library #6) | $1.7 \times 10^{10}$ | $9.75 \times 10^{10}$ |

DNA from purified NNN and EGG master libraries were isolated, their segments bearing permutated capsid genes were amplified using PCR-mediated protocol and subcloned into pBluescript plasmid (pBS). Random clones (7 for NNN and 9 for EGG) were sequenced and aligned using Vector NTI Suit software. All seven clones from the NNN library contain random hepta-peptide sequence inserted downstream of WT AAV2 $R_{585}$. At the same time, EGG library clones contain EGG triplets embedded into the random sequence. The insertion of a random hepta peptide moves the second Arg residue from position 588 in WT parent to a position 595 in a library's vectors, rendering them negative for HSPG binding. As expected, master libraries failed to bind to heparin-sepharose column, indicating a loss of affinity towards HSPG receptor. Therefore, these experiments clearly demonstrate the technical feasibility of constructing combinatorial libraries using the protocols described herein.

Example 6

Modifying AAV Capsids Using Degenerate Synthetic Oligonucleotides

Computer modeling of the AAV2 (Xie et al., Proceedings of the National Academy of Sciences 99:10405–10410, 2002) and AAV4 atomic structures revealed 7 hypervariable regions that are presumably exposed to the surface of the capsid. The initial analysis was described recently by Opie et al. (J. Virol. 77:6995–7006, 2003). Degenerative positions were derived upon alignment of the VP1 sequences of AAV serotypes 1 through 8. The strategy employed to modify the hypevariable region of 1.4 Kbp was based on simultaneously mutagenizing sequences coding for 7 surface loops. The method used to synthesize degenerate capsid genes of the invention is similar to the protocol described by W. Coco et al. (Nature Biotechnology 20:1246–1250, 2002) except the 3' amino group of the bottom (scaffold) strand was not modified. This allowed the generation of a full-length double-stranded modified fragment which could be purified using standard agarose gel electrophoresis/purification protocols. This resulted in greater yields of the purified degenerate fragment.

To mutagenize sequences coding for 7 surface loops, a first pair of oligonucleotides homologous to the WT AAV2 cap sequence to be amplified (beginning with L1) were synthesized. These two oligonucleotides are non-contiguous, in that there is a gap between the two oligonucleotides. Any oligonucleotides that are homologous to at least a portion of the hypervariable region may be used as a first set of oligonucleotides in a protocol for mutagenizing the hypervariable region. These two oligonucleotides were added to an in vitro reaction containing a third oligonucleotide. The third oligonucleotide shares some level of homology to the sequence encompassed by the gap, but includes polymorphisms from other AAV serotypes (e.g., degeneracies). This third oligonucleotide is complementary to and therefore anneals to the ends of the first two oligonucleotides, resulting in a gap in the top strand as well as two over-hangs on the bottom strand. The polymerase fills in the gap, and extends the two overhangs, resulting in a double-stranded extension product (FIG. 2). The partially overlapping first set of oligonucleotides were designed so that gaps to be filled by polymerase incorporated degeneracies corresponding to every polymorphism within the 7 loops of AAV capsid genes serotypes 1 through 8. The extension product was purified and annealed to a fourth overlapping oligonucleotide and the extension/purification step was repeated. Fragments incorporating L2–L4, L5–6 and L7 were synthesized in a similar fashion by sequentially adding more overlapping oligonucleotides and purifying the extension product using agarose gel electrophoresis (FIG. 3). The final product (fragment incorporating L1–L7) was amplified using PCR and subcloned into pTR-AAV2 using ApaI-EagI restriction enzymes, generating a vector library containing degenerate VP1 capsid genes. This DNA was used to transfect Sf9 cells and generate rcAAV2-pseudotyped "seed" library, as shown in FIG. 1.

Example 7

Alternative Degenerate Oligonucleotide Synthesis Strategy

In an alternative strategy for mutagenizing the L1 through L7 regions of the AAV2 cap gene, the following protocol may be employed.

1. Mutagenize ApaI at nucleotide 4049
2. Introduce EagI
3. PCR AgeI-BssHII (approximately 200 bp, designate AB) and AatII-SpeI (approximately 330 bp, designate AS) fragments
4. Subject L1 through L7 fragments to degenerate oligonucleotide mutagenesis 5. Cut L1 and AB with AgeI, ligate, purify LI-AB
6. Cut L1-AB and L2–L4 with BssHII, ligate, purify L1–AB–L2–L4 fragment
7. Cut L5-L6 and AS with AatII, ligate, purify L5–L6–AS fragment
8. Cut L5-L6–AS and L7 with SpeI, ligate, purify L5–L6–AS–L7
9. Cut #6 and #8 with NcoI, ligate, purify 1.4 Kb fragment
10. The resultant fragment is restriction digested with ApaI (at nucleotide 4049) and EagI. This fragment is then cloned into a desired vector for transfer into a host cell.

Example 8

Viability Index of Viral Library

Molecular breeding of AAV capsid genes is based on the assumption that some sub-population of modified capsid proteins will be capable of forming viable virions, and that some of those virions will display a new tropism towards cell surface receptors. Assuming that the fraction of viable clones is reasonably high (e.g. 1–10%) one might expect to build a "Universal Master Library" having complexity high enough to display any desirable cell specificity. The construction of a "Universal Master Library" is possible considering the diverse source of naturally-evolved members of the Parvovirdae family (Lukashov et al., J. Virol. 75:2729–2740, 2001). Each of the 41 individual species can be used as a shuffling donor in a gene shuffling protocol (e.g., RATCHITT) or can be used to derive degenerate oligonucleotides for a degenerate oligonucleotide synthesis protocol. Such a library would represent an extremely useful reagent to derive a new generation of targeted virions for gene therapy. In order to estimate practical limits of breeding technology as applied for AAV evolution, a viability index of a library containing shuffled capsid genes of closely related AAV1 and AAV2 will be evaluated.

Viability of chimeric virions will be evaluated by their ability to rescue, replicate and package into modified (e.g., degenerate, shuffled) capsids. Specifically, this will be done by titering crude preparations of virions using a real time PCR protocol and unshuffled parent vectors as positive controls. The viability index will then be adjusted for to construct a chimeric plasmid library with a complexity of at least $10^6$ viable clones.

Example 9

Production and Titering of Virions Containing Shuffled Genes

If a particular shuffled capsid gene encodes a viable capsid, cells transfected with TR-containing plasmid (as shown at the top in FIG. 1A) produce virions containing DNAseI-resistant single-stranded viral DNA that can be titered using regular protocols upon treatment of such preparation with DNAseI. Vector DNAs from 20 clones are characterized by sequencing and are co-transfected with pXX6 mini-Ad helper (Xiao and Samulski, J. Virol 72:2224–2232, 1998) into HEK 293 cells using a standard Ca-phosphate-mediated protocol. Forty eight hours post-transfection cells are harvested and crude lysate is prepared as described (Zolotukhin et al., Gene Ther. 6:973–985, 1999; and Potter et al., Methods Enzymol in press, 2002). Subsequently, those lysates are treated with DNAse I and titered using real-time PCR, as described (Potter et al., Methods Enzymol in press, 2002). The primer set for this assay is designed to amplify the region within the rep gene of the vector, which is not mutagenized by shuffling. Forward primer: CGCGAAAAACTGATTCAGAGAA (SEQ ID NO:8) ($T_m$ of 58° C., WT AAV2 coordinates 657–678); Reverse primer: GACCGCGAACCAGTTTGGC (SEQ ID NO:9) ($T_m$ of 59° C., WT AAV2 coordinates 705–722); TaqMan Probe: CCGCGGGATCGAGCCGAC (SEQ ID NO:10) ($T_m$ of 68° C., WT AAV2 coordinates 683–700). A three step PCR is performed for 35 cycles; denaturation is at 94° for 20 seconds; annealing is performed at 55° C. for 20 seconds; and extension is performed at 72° C. for 30 seconds.

An estimate of 1–10% of viable recombinants is a rather conservative target viability index estimate; this number will be a function of the region subjected to shuffling. If no packageable clones are originally isolated, more clones are characterized for the viability index. If the strategy implemented to shuffle the most homologous parts of the VP1, VP2, and VP3 genes results in a low (<1%) yield of viable clones, the shuffling range is narrowed down to include only VP1 and VP2 N-terminal domains. This strategy maintains the VP3 structure of the donor vector intact, thereby increasing the capsid viability.

Example 10

Demonstration of the Utility of a Shuffled Library

The ideal library should contain sufficient complexity/diversity to allow the selection of a virion targeted to a particular cell population. The master library is utilized to select for recombinants with a particular tropism.

Some cell lines are naturally resistant to infection by recombinant or WT AAV2. These include the human leukemic cell line UT-7/Epo (Mizukami et al., Virology 217: 124–130, 1996) and the human megakaryocytic leukemia cell lines MB-02 and MO7e (Ponnazhagan et al., J. Gen. Virol. 77 (pt 6):1111–1122, 1996). The inability of AAV2 to bind to these cells is consistent with a reduced or absent cellular expression of AAV receptor (Bartlett et al., Nat Biotechnol. 17:181–186, 1999). Based on this information, MO7e target cells are used as a model system for selecting modified rAAV vectors in the library displaying a random NNN motif (library #6 Table 1). Specifically, $10^6$ MO7e cells grown in a flask are infected with a $10^8$ drp aliquot from a master library for 1 h (MOI of 100 drp/cell), cells are washed with media, and fresh media containing AdS is added to supplement contaminating Ad (combined MOI of 5). Simultaneously, two more flasks are infected with WT AAV1 and WT AAV2 virions with the same MOI and conditions as described for the library. Forty eight hours post-infection cells are harvested, washed with PBS and virions are purified using an iodixanol gradient as described above. AAV and Ad virions in three preparations (shuffled library, WT AAV 1 and WT AAV2) are titered by real-time PCR assay and dot-blot assay, and the cycles of infection/harvesting/purification/titering are repeated until sufficient rcAAV shuffled vector is propagated to isolate at least 1 µg of viral DNA. This viral DNA is used to amplify and sub-clone the modified DNA segment using a PCR-mediated protocol. Individual clones are characterized by sequencing.

The master library is used to select a virion specific for unrelated target—mouse embryonic stem cells (MESC). MESC are non-transformed, primitive cells that are derived from the inner cell mass of 3.5-day post coitus blastocysts and are capable of differentiating into numerous types of cells. The cells of the inner cell mass are considered pluripotent, in that each is capable of producing multilineage descendants. The resulting progeny are representative of the differentiated cell types of ectoderm, mesoderm, endoderm, and even the germ line when reintroduced into host blastocysts (van der Kooy and Weiss, Science 287:1439–1441, 2000). Embryonic stem cells also have the capacity for prolonged self-renewal (Bradley A., Curr. Opin. Cell Biol. 2: 1013–1017, 1990). rAAV-GFP pseudotyped in either type 1, 2, or 5 AAV capsids were not able to transduce these target cells even at an MOI up to $10^4$, even though MESC were efficiently infected with rAd-GFP. Therefore, MESC are used as a target cell line to select for virions able to infect a cell line non-permissible to WT AAV infections.

As another demonstration of the utility of the combinatorial libraries to select for vectors with a desired tropism, a culture of primary human adipocytes and four libraries displaying pre-screened motifs specific for adipocytes (Arap et al., Nature Medicine 8:121–127, 2002) are used. Methods of preparing and culturing primary human adipocytes have been extensively described (see Fried et al., Culture of Adipose Tissue and Isolated Adipocytes. New Jersey: Humana Press, 2001). Upon several rounds of reiterative selection using four independent libraries (libraries 1, 2, 3 and 5 of Table 1), a population of AAV vectors are propagated that is capable of establishing a productive infection in primary adipocyte cultures. WT AdS helper virus is used to co-infect cells at an MOI of 5. AAV viral DNA is purified and the modified portion of the genome is amplified and sub-cloned using a PCR-mediated protocol. Sequencing and restriction analysis determines the complexity of the selected population. The major species is cloned into TR-less plasmid backbones to produce helper plasmids. This helper is used to pseudotype rAAV2 vectors encoding the GFP reporter gene and featuring a newly acquired tropism to human adipocytes.

Example 11

Virions Containing Shuffled Genomes and Particular Tropisms

Upon several rounds of reiterative selection a population of virions are propagated that are capable of establishing a productive infection in an otherwise non-permissive cell line (MO7e). Viral DNA is purified and the shuffled portion of the genome is amplified and cloned using a PCR-mediated protocol. Sequencing and restriction analysis determines the complexity of the selected population. The major species are subcloned into TR-less plasmid backbones to produce a helper similar to pACG2r1c, or pACG2r5c (See FIG. 4). This new helper/s is used to pseudotype a rAAV2 vector encoding a GFP reporter gene and featuring a newly acquired tropism to a particular cell line.

To demonstrate selection for a virion that has an enhanced tropism to a known, previously characterized cell surface marker, a virion having a tropism to the human long-form leptin receptor (Ob-$R_L$) is selected. It was shown that among different cell populations in the brain, neurons are the primary targets for rAAV-mediated gene expression. However, not all neurons are permissive to infection with rAAV. The problem could be partially alleviated using different AAV serotypes. Nevertheless, it would be highly desirable to be able to target specific population of neurons for a particular application, e.g. Ob-$R_L$-expressing neurons in the hypothalamus that are targets for hormone leptin (obesity), or dopaminergic neurons in substantia nigra (Parkinson's disease). Using the approaches described below, evolved virions that specifically bind to Ob-RL marker are selected for, mimicking to some extent a ligand/receptor interaction. Such an interaction, though, is different in a way that it is followed by the internalization of the ligand (viral particle), since only productively infectious particles will be selected for. In this regard the initial virion/receptor interaction requires a subsequent putative co-receptor involvement for the particle to be internalized. To achieve this goal, the two following independent approaches are employed.

1. The sequence encoding hormone leptin is integrated into the shuffling mix, utilizing recombination protocols that are independent of parents' homology. Fragments of leptin molecule are incorporated into the capsid structure of the virion. Such a chimeric library generates a species exposing leptin epitopes that interact with Ob-$R_L$ receptor. For the purpose of incorporating leptin epitopes a variable region of VP3 capsid protein is utilized.

2. As an alternative approach, a new selection protocol, "subtractive binding", is used. It is based on an immortalized GT1-7 neuronal cell line (Mellon et al., Neuron 5:1–10, 1990), a clonal differentiated GnRH neurosecretory cell line derived from an SV40 T-antigen-expressing tumor of the mouse hypothalamus. GT1-7 cells do not express Ob-$R_L$ and are unresponsive to leptin stimulation (White et al., Proceedings of the National Academy of Sciences 94: 10657–10662, 1997). However, introduction of the cDNA encoding Ob-$R_L$ into GT1-7 neurons has shown that these cells express the appropriate signal transduction apparatus to support ligand-induced Ob-$R_L$ transcriptional regulation (White et al., Proceedings of the National Academy of Sciences 94:10657–10662, 1997). High-level expression of leptin receptor was achieved by infecting these cells with recombinant Ad-Ob-$R_L$ encoding the long form of leptin receptor. A recombinant Ad encoding human Ob-$R_L$ was constructed. This model system is used to select for Ob-$R_L$-specific virions using the following protocol. First, one T75 flask ($10_7$) of GT1-7 cells is infected with $10^8$ particles from the master library and the infection proceeds for 24 hrs. Simultaneously, GT1-7 cells seeded in a similar flask are infected with rAd-Ob-$R_L$ (MOI of 5). One hour post-infection the media in flask 2 is changed and rAd-infected cells are allowed to incubate for another 23 hrs until Ob-$R_L$ encoded by the rAd genome is fully expressed and functional. By that time the rcAAV shuffled library in flask 1 is exhausted by the pool of potential receptors on the surface of GT1-7, and consists of an "enriched" population of virions that bind only to a new set of receptors not present on GT1-7, e.g. Ob-$R_L$. At this time the media with a "subtracted" library is transferred into the flask 2, and pre-infected with rAd-Ob-$R_L$. Any particles having the newly acquired affinity toward Ob-$R_L$, get attached and, hopefully, internalized by the cell. Such a rAAV population is then propagated and analyzed, as described in the first paragraph of Example 9. To reduce the background inevitably accompanying such screenings, the enriched viral population is passed through an unrelated cell line (HEK 293) following an identical protocol and utilizing rAd-Ob-$R_L$.

Based on the knowledge acquired during the construction of an AAV1-2 shuffled library, strategies are developed for recombining serotypes 1 through 5 using different combinations of parent genomes. Shuffled libraries based on pairwise recombinations of AAV serotypes 1 through 5 are constructed, as well as combinations thereof. These shuffled AAV libraries are used to select virions with new or altered cellular tropisms, as described above.

TABLE 2

| | Pairwise comparison of capsid genes of AAV serotypes 1 through 5. | | | | |
|---|---|---|---|---|---|
| | AAV1 capsid (%) | AAV2 capsid (%) | AAV3 capsid (%) | AAV4 capsid (%) | AAV5 capsid (%) |
| AAV1 capsid | 100 | 80 | 80 | 67 | 62 |
| AAV2 capsid | | 100 | 81 | 66 | 62 |
| AAV3 capsid | | | 100 | 67 | 62 |
| AAV4 capsid | | | | 100 | 60 |
| AAV5 capsid | | | | | 100 |

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A non-naturally occurring nucleic acid comprising:

(A) a first nucleotide sequence encoding at least one AAV Rep protein; and (B) a second nucleotide sequence encoding at least one AAV Cap protein, wherein the second nucleotide sequence comprises (i) a polynucleotide encoding a portion of a Cap protein found in an AAV of a first serotype but not in an AAV of a second serotype differing from the first serotype and (ii) a polynucleotide encoding a portion of a Cap protein found in the AAV of the second serotype, but not in the AAV of the first serotype, wherein the non-naturally occurring nucleic acid further comprises a first AAV TR and a second AAV TR, and the first and second nucleotide sequences are interposed between the first and the second AAV TRs.

2. The non-naturally occurring nucleic acid of claim 1, wherein the first and the second AAV TRs are from serotype 2.

3. The non-naturally occurring nucleic acid of claim 1, wherein the first serotype is serotype 1.

4. The non-naturally occurring nucleic acid of claim 1, wherein the first serotype is serotype 2.

5. The non-naturally occurring nucleic acid of claim 1, wherein the first serotype is serotype 3.

6. The non-naturally occurring nucleic acid of claim 1, wherein the first serotype is serotype 4.

7. The non-naturally occurring nucleic acid of claim 1, wherein the first serotype is serotype 5.

8. The non-naturally occurring nucleic acid of claim 1, wherein the first serotype is serotype 6.

9. The non-naturally occurring nucleic acid of claim 1, wherein the first serotype is serotype 7.

10. The non-naturally occurring nucleic acid of claim 1, wherein the first serotype is serotype 8.

11. The non-naturally occurring nucleic acid of claim 1, wherein the nucleic acid is comprised within a vector.

12. The non-naturally occurring nucleic acid of claim 1, wherein the AAV Rep protein is from serotype 2.

13. The non-naturally occurring nucleic acid of claim 1, wherein the nucleic acid further comprises a third nucleotide sequence encoding at least one molecule providing helper function.

14. The non-naturally occurring nucleic acid of claim 13, wherein the third nucleotide sequence encoding at least one molecule providing helper function is a polynucleotide from a virus selected from the group consisting of: adenovirus and herpesvirus.

15. A vector library comprising at least a first vector and a second vector, the first vector comprising a nucleic acid comprising:

(A) a first nucleotide sequence encoding at least one AAV Rep protein; and (B) a second nucleotide sequence encoding at least one AAV Cap protein, wherein the second nucleotide sequence comprises (i) a polynucleotide encoding a portion of a Cap protein found in an AAV of a first serotype but not in an AAV of a second serotype differing from the first serotype, and (ii) a polynucleotide encoding a portion of a Cap protein found in the AAV of the second serotype, but not in the AAV of the first serotype, wherein the nucleic acid further comprises a first AAV TR and a second AAV TR, and the first and second nucleotide sequences are interposed between the first and the second AAV TRs, and the second vector differing from the first vector by at least one nucleotide.

16. The vector library of claim 15, wherein the vector library is incorporated into at least one host cell.

17. The vector library of claim 16, wherein the host cell is an insect cell.

18. An AAV virion comprising a nucleic acid comprising:

(A) a first nucleotide sequence encoding at least one AAV Rep protein;

(B) a second nucleotide sequence encoding at least one AAV Cap protein, wherein the second nucleotide sequence comprises (i) a polynucleotide encoding a portion of a Cap protein found in an AAV of a first serotype but not in an AAV of a second serotype differing from the first serotype, and (ii) a polynucleotide encoding a portion of a Cap protein found in the AAV of the second serotype, but not in the AAV of the first serotype; and (C) a first and a second AAV TR, wherein the first and the second nucleotide sequences are interposed between the first and the second AAV TRs.

19. The AAV virion of claim 18, wherein the first and second TRs are from serotype 2.

20. The AAV virion of claim 18, wherein the virion comprises an AAV Cap protein.

21. The AAV virion of claim 18, wherein the AAV Rep protein is from serotype 2.

22. The AAV virion of claim 18, wherein the AAV virion is incorporated into a host cell.

23. The AAV virion of claim 18, further comprising at least one AAV Cap protein encoded by the second nucleotide sequence.

24. The AAV virion of claim 20, wherein the Cap protein is a WT Cap protein.

25. The AAV virion of claim 20, wherein the second nucleotide sequence further comprises a polynucleotide encoding a portion of a Cap protein found in an AAV of a third serotype but not found in a Cap protein of an AAV of the first or second serotypes.

26. The AAV virion of claim 24, wherein the WT AAV Cap protein is from serotype 2.

27. The AAV virion of claim 25, wherein the second nucleotide sequence further comprises a polynucleotide encoding a portion of a Cap protein found in an AAV of a fourth serotype but not found in a Cap protein of an AAV of the first, second or third serotypes.

28. The AAV virion of claim 27, wherein the second nucleotide sequence further comprises a polynucleotide encoding a portion of a Cap protein found in an AAV of a fifth serotype but not found in a Cap protein of an AAV of the first, second, third or fourth serotypes.

29. The AAV virion of claim 28, wherein the second nucleotide sequence further comprises a polynucleotide encoding a portion of a Cap protein found in an AAV of a sixth serotype but not found in a Cap protein of an AAV of the first, second, third, fourth or fifth serotypes.

30. The AAV virion of claim 29, wherein the second nucleotide sequence further comprises a polynucleotide encoding a portion of a Cap protein found in an AAV of a seventh serotype but not found in a Cap protein of an AAV of the first, second, third, fourth, fifth or sixth serotypes.

31. The AAV virion of claim 30, wherein the second nucleotide sequence further comprises a polynucleotide encoding a portion of a Cap protein found in an AAV of an eight serotype but not found in a Cap protein of an AAV of the first, second, third, fourth, fifth, sixth or seventh serotypes.

32. The AAV virion of claim 22, wherein the host cell is a mammalian cell.

33. The AAV virion of claim 23, wherein the TRs are from AAV serotype 2.

34. An AAV virion comprising:

(A) a nucleic acid comprising:

(i) a first AAV TR;

(ii) a second AAV TR;

(iii) a non-AAV nucleic acid interposed between the first AAV TR and the second AAV TR; and (B) at least one AAV Cap protein, wherein the Cap protein is encoded by a nucleotide sequence comprising nucleic acid sequences from AAVs of at least a first serotype and a second serotype differing from the first serotype and interposed between the first and the second AAV TRs.

35. The AAV virion of claim 34, wherein at least one of the TRs is from AAV serotype 2.

36. The AAV virion of claim 34, wherein the nucleotide sequence further comprises a nucleic acid sequence from an AAV of a third serotype differing from the first and second serotypes.

37. The AAV virion of claim 34, wherein the nucleic acid further comprises an expression control sequence.

38. The AAV virion of claim 34, wherein the non-AAV sequence encodes a therapeutic molecule.

39. The AAV virion of claim 34, wherein the virion is incorporated into a host cell.

40. The AAV virion of claim 36, wherein the nucleotide sequence further comprises a nucleic acid sequence from an AAV of a fourth serotype differing from the first, second, and third serotypes.

41. The AAV virion of claim 40, wherein the nucleotide sequence further comprises a nucleic acid sequence from an AAV of a fifth serotype differing from the first, second, third and fourth serotypes.

42. The AAV virion of claim 41, wherein the nucleotide sequence further comprises a nucleic acid sequence from an AAV of a sixth serotype differing from the first, second, third, fourth and fifth serotypes.

43. The AAV virion of claim 42, wherein the nucleotide sequence further comprises a nucleic acid sequence from an AAV of a seventh serotype differing from the first, second, third, fourth, fifth, and sixth serotypes.

44. The AAV virion of claim 43, wherein the nucleotide sequence further comprises a nucleic acid sequence from an AAV of a eight serotype differing from the first, second, third, fourth, fifth, sixth, and seventh serotypes.

45. The AAV virion of claim 37, wherein the expression control sequence effects tissue-specific expression of the non-AAV nucleic acid.

46. The AAV virion of claim 37, wherein the expression control sequence comprises a promoter operably linked to the non-AAV nucleic acid.

47. The AAV virion of claim 38, wherein the therapeutic molecule is selected from the group consisting of: a polypeptide and a RNA.

48. The AAV virion of claim 39, wherein the host cell is a mammalian cell.

49. The AAV virion of claim 48, wherein the mammalian cell is a human cell.

50. A virion library comprising at least a first AAV virion and a second AAV virion, the first AAV virion comprising a nucleic acid comprising:

(A) a first nucleotide sequence encoding at least one AAV Rep protein;

(B) a second nucleotide sequence encoding at least one AAV Cap protein, wherein the second nucleotide sequence comprises (i) a polynucleotide encoding a portion of a Cap protein found in an AAV of a first serotype but not in an AAV of a second serotype differing from the first serotype, and (ii) a polynucleotide encoding a portion of a Cap protein found in the AAV of the second serotype, but not in the AAV of the first serotype; and (C) a first and a second AAV TR, wherein the first and the second nucleotide sequences are interposed between the first and the second AAV TRs, and the second AAV virion comprising a nucleic acid not comprised within the first AAV virion.

51. The virion library of claim 50, wherein the TRs are from serotype 2.

52. The virion library of claim 50, wherein the first and the second virions both comprise at least one WT AAV Cap protein.

53. The virion library of claim 50, wherein the virions are incorporated into at least one host cell.

54. The virion library of claim 50, the first and second virions further comprising at least one AAV Cap protein encoded by the second nucleotide sequence, wherein the second AAV virion comprises a Cap protein not comprised within the first AAV virion.

55. The virion library of claim 53, wherein the host cell is an insect cell.

56. The virion library of claim 53, wherein the host cell is a mammalian cell.

* * * * *